(12) United States Patent
Chedid et al.

(10) Patent No.: US 7,068,054 B2
(45) Date of Patent: Jun. 27, 2006

(54) REAL-TIME CARBON SENSOR FOR MEASURING CONCENTRATION PROFILES IN CARBURIZED STEEL

(75) Inventors: Loutfallah Georges Chedid, West Newton, MA (US); Makhlouf M. Makhlouf, Shrewsbury, MA (US); Richard D. Sisson, Jr., Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 351 days.

(21) Appl. No.: 10/373,663

(22) Filed: Feb. 24, 2003

(65) Prior Publication Data
US 2004/0016652 A1 Jan. 29, 2004

Related U.S. Application Data

(60) Provisional application No. 60/385,256, filed on Jun. 1, 2002.

(51) Int. Cl.
*G01R 27/08* (2006.01)
*G01N 27/04* (2006.01)

(52) U.S. Cl. .................. 324/717; 324/448
(58) Field of Classification Search ............... 324/717, 324/448, 697, 691–693, 724, 707
See application file for complete search history.

(56) References Cited

U.S. PATENT DOCUMENTS

| | | | | |
|---|---|---|---|---|
| 3,487,301 | A * | 12/1969 | Gardner et al. | 324/717 |
| 4,068,168 | A * | 1/1978 | Boonstra | 324/722 |
| 6,566,636 | B1 * | 5/2003 | Bentley et al. | 219/665 |
| 6,788,076 | B1 * | 9/2004 | Howland | 324/717 |
| 2005/0068047 | A1 * | 3/2005 | Claus | 324/693 |

OTHER PUBLICATIONS

A. Matthiessen et al., "Ueber den Einfluss der Temperature auf die elektrische Leitungsfahigkeit der Legirungen", Annalen der Physick und Chemie, Funfte Reihe, Zweiter Band, ed. J.C. Poggendorff, Johann Abrosius Barth (Leipzig 1864), p. 19-78.

E.D. Campbell et al., "The Specific Resistance and Thermo-Electromotive Potential of Some Steels Differing Only in Carbon Content", J. Iron Steel Inst., vol. CXIII, No. 1, p. 375-392.

(Continued)

*Primary Examiner*—Anjan Deb
(74) *Attorney, Agent, or Firm*—R. Dennis Creehan, Esq.

(57) ABSTRACT

An alloy solute sensor probe, measurement system and measurement method are disclosed for directly measuring solute concentration profiles in conductive material components at elevated processing temperatures. The disclosed device and method permit direct, real-time non-destructive measurement of solute concentration profiles in treated surfaces in alloy components. In disclosed embodiments, a novel concentric carbon sensor and rod-shaped carbon sensor are disclosed which employ AC frequencies for probing the subsurface region of alloy samples to determine carbon concentration profiles at steel surfaces from measurements of alloy resistivity profiles. Results of carbon profile measurements obtained with the disclosed device and method compare favorably with conventional destructive analytical measurements made on post-processed samples. The sensor probe and method may be utilized to determine solute concentration profiles with a variety of solute materials and alloy compositions and may be advantageously employed in alloy surface processing, carburization heat treatments, induction heating and fatigue fracture applications.

28 Claims, 22 Drawing Sheets

OTHER PUBLICATIONS

R.M. Bozorth, Ferromagnetism, Van Nostrand (Princeton 1951) p. 367.

F. Bitter, Currents, Fields and Particles, MIT Technology Press/John Wiley (New York 1956), p. 100-110.

B.R. Tittmann et al., "Measurement of Physical Property Gradients with Elastic Surface Wave Dispersion", Proc. 9th Symp. on Nondestructive Evaluation, Apr. 25-27, 1973, San Antonio, TX, Amer. Soc. for Nondestructive Testing/Southwest Research Inst., p. 20-28 (1973).

M. Pancholy et al., "Ultrasonic Attenuation in Carbon Steels", Indian J. Technology, vol. 19, p. 493-498, Dec. 1981.

B.R. Tittmann et al., "Determination of Physical Property Gradients from Measured Surface Wave Dispersion", IEEE Trans. vol. UFFC-34, No. 5, p. 500-507, Sep. 1987.

R.D. Mitra, "Case Depth Evaluation of Carburized Specimens Using Ultrasonic Methods", S.B./S.M. Thesis, M.I.T. (Cambridge 1993).

S. Vaidyanathan, "Evaluation of Carburization Depth in Service Exposed Ferritic Steel Using Magnetic Barkhausen Noise Analysis", Proc. 14th World Conf. on NDT, New Delhi, India, Dec. 8-13, 1996, Trends in NDE Science and Technlogy, vol. 3,, ed. C.G. Krishnadas Nair et al., A.A. Balkema (Rotterdam 1997), p. 1639-1642.

* cited by examiner (a)
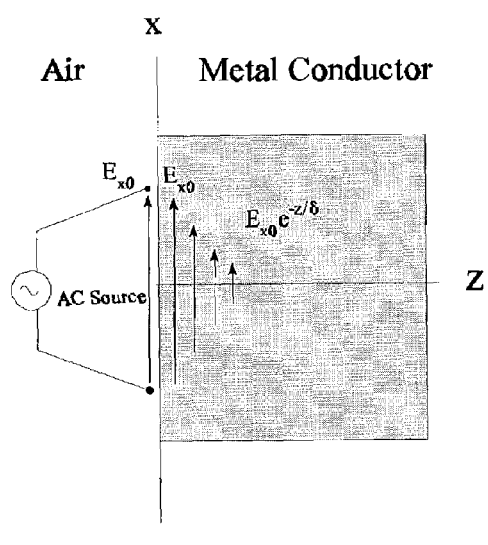
(b)
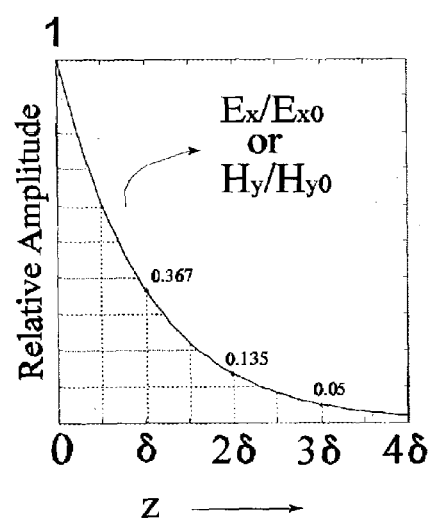
FIG. 2A
FIG. 2B

REAL-TIME CARBON SENSOR FOR MEASURING CONCENTRATION PROFILES IN CARBURIZED STEEL

CROSS-REFERENCES

This application claims the benefit under 35 U.S.C. 119(e) of co-pending U.S. provisional patent application U.S. Ser. No. 60/385,256 filed on Jun. 1, 2002 which is incorporated herein by this reference.

FIELD OF THE INVENTION

This invention relates to devices and methods for measuring carbon concentration profiles in metal alloys. More particularly, this invention relates to an electronic carbon sensor, a carbon sensing system and non-destructive, real-time method for direct measurement of carbon concentration profiles in steel alloys during alloy processing at carburization temperatures.

BACKGROUND OF THE INVENTION

The metals heat treating industry in the United States is a $20 billion industry. Globally, heat treating represents nearly $75 billion or more in value added to manufacturing. The process of carburizing alloys is estimated to account for about twenty percent of heat treating activities. Carburized parts are essential to the fabrication and operation of components in transportation, aerospace, defense, construction, chemical and materials, industrial processing and heavy equipment industries.

Carburizing is a surface treatment which produces a hard surface on steels due to the reaction of carbon containing gases with the alloy surface and diffusion of carbon into the alloy to form a hardened surface layer commonly referred to as a case. In a typical carburizing process, austenitic steel is brought into contact with an atmosphere having sufficient carbon potential to cause absorption of carbon at the alloy surface and diffusion of carbon into the alloy to create a carbon concentration gradient between the alloy surface and interior [see *Carburizing and Carbonitriding*, American Society for Metals (Metals Park, Ohio) 1977; *Metals Handbook: Heat Treating*, vol. 4, 9$^{th}$ ed., American Society for Metals (Metals Park, Ohio) 1981, p 135, p. 417–431; W. Hume-Rothery, *The Structures of Alloys of Iron*, Pergamon Press (Oxford, England) 1966]. The shape and depth of the carbon concentration profile in the surface layer depends largely on the duration of the carburizing cycle, the temperature of the cycle, and the carbon potential in the atmosphere. The carbon concentration gradient and subsequent quenching process determine the final structure and properties of the carburized surface layer.

The development of conventional carburizing process sensors, computerized control systems, and on-line process modeling have increased the quality of heat treating with respect to accuracy and reproducibility of carburizing processes and case hardened alloys [see B. Edenhofer, "Carburizing and Nitriding Industry in the Eastern Hemisphere". *Proceedings of the Second International Conference on Carburizing and Nitriding with Atmospheres*, 6–8 Dec. 1985, Cleveland, Ohio. ASM, 1985, Page 3–8; Z. Wang, and J. Zhang, "Precise Control of Gas Carburizing Process by Microprocessor". *Proceedings of International Heat Treating Conference: Equipment and Processes*, 18–20 Apr. 1994, Schaumberg, Ill. p. 479–482. ASM 1994; Karlo Raie, "Control of Gas Carburizing by the Diagram Method". *Scandinavian Journal of Metallurgy* (1993), 22, p. 50–54; T. Reti, M. Reger, and M. Gergely, "Computer Prediction of Process Parameters of Two-Stage Gas Carburizing". *J. Heat Treating*, Vol. 8, No.1, 1990, p. 55–61; T. Guler, "Optimizing Gas Carburizing Atmospheres with a Supervisory On-Line Carbon Diffusion Control System." *Industrial Heating*. January 1997. p. 31–34].

Since their introductions in the early 1970's, oxygen sensors or probes have become the tool of choice for control of carbon potential in carburizing applications [see U.S. Pat. Nos. 3,454,486, 3,546,086, 3,596,345, 4,101,404, 4,193,857, 4,588,493; British Patent 4,101,404;] [B. Edenhofer, *Proceedings of the Second International Conference on Carburizing and Nitriding with Atmospheres*, 6–8 Dec. 1985, Cleveland, Ohio. ASM, 1985, p. 3–8; D. W. McCurdy, "Improving the Accuracy of Oxygen Probe Control Systems". *Proceedings of International Heat Treating Conference: Equipment and Processes*, ASM. 18–20 Apr. 1994. Schaumberg, Ill., p. 117–121]. These conventional sensors provide measurements of the carbon potential in the atmosphere by measuring the oxygen partial pressure and converting it into carbon potential. This capability has introduced significant improvement in the control of carburizing processes. However, due to their reliance on gas phase measurements and subsequent conversion to carbon potentials these sensors are susceptible to problems with carbon sooting, catalytic effects, and oxygen reference potential problems, leading to undetected drift and poor failure detection [see D. W. McCurdy, *Proceedings of International Heat Treating Conference: Equipment and Processes*, ASM. 18–20 Apr. 1994. Schaumberg, Ill., p. 117–121; M. Howes, *Proceedings of the Second International Conference on Carburizing and Nitriding with Atmospheres*, 6–8 Dec. 1985, Cleveland, Ohio. Pages 9–13. ASM 1985.; R. N. Blumenthal, "A Technical Presentation of the Factors Affecting the Accuracy of Carbon/Oxygen Probes." *ASM's 1995 Conference Proceedings on Carburizing and Nitriding with Atmospheres*. Cleveland, Ohio, p. 17–22]. Additionally, although these probes may measure the oxygen potential in a furnace atmosphere accurately and convert this to carbon potential, this is an indirect measurement of the actual carbon potential and no information is provided regarding the actual carbon concentration or concentration profile in the alloy. As a direct result, over carburization of alloys by 10 to 15% is a commonly encountered practice in commercial processes. Consequently, inaccurate control of the carbon profile in the surface layers of processed alloys leads to loss of parts due to treated components which fail to meet specific case hardened alloy specifications.

It is most advantageous for the heat treating industry to have the means to establish and maintain appropriate process parameters for both the introduction and transport of carbon into alloy surfaces during carburization for proper process control to produce desirable carbon concentration profiles [see T. Reti, M. Reger and M. Gergely, "Computer Prediction of Process Parameters of Two-Stage Gas Carburizing". *J. Heat Treating*, Vol. 8, No.1, 1990, p. 55–61; R. Fincken, "Selecting Process Controls." *Advanced Materials & Processes*, vol. 155, No. 6, June 1999, p. H39–H41]. Initially, during a carburization boost stage, carbon is adsorbed in the surface layer of the processed alloy using a high carbon potential in the furnace atmosphere. In a subsequent diffuse stage, the furnace temperature and carbon potential are lowered and carbon diffuses into the steel to create a carburized surface layer. These combined treatments produce a finite and distinct carbon concentration profile in the surface layer of the processed alloy. Unfortunately, the process control of the resultant carbon profiles is significantly compromised due to the lack of a real-time direct measurements of the actual carbon profiles in the processed alloy and the inability to accurately determine the appropriate transition point between the boost and the diffuse stages [see B. Edenhofer, "Process Control of Gas Carburizing Heat Treatment of Metals", *Heft* 4, 1985, p. 87–91; J. J. Bausch, L. G. Chedid, and R. D. Sisson, "The Design of a Fully Automated Control System for Gas Carburization." *ASM's* 1995 *Conference Proceedings on Carburizing and Nitriding with Atmospheres*. Cleveland, Ohio, p. 23–28].

Due to the shortcomings of conventional gas phase sensors in measurement and control of carbon concentration profiles in carburization processes, a number of workers have evaluated alternative devices for measuring carbon concentration profiles in alloy materials. Moorthy, et al. reported the use of Magnetic Barkhausen Noise (MBN) measurements for room temperature measurement of the thickness of case hardened surfaces [see V. Moorthy, et al. "Evaluation of Carburization Depth in Service Exposed Ferritic Steel Using Magnetic Barkhausen Noise Analysis." *Trends in NDE Science & Technology; Proceedings of the 14$^{th}$ World Conference on Non-Destructive Testing*, New Delhi, 8–13 Dec. 1996. Vol.3, p. 1639–1642]. Moorthy found that this method was unsuitable for measurement of carbon profiles in alloys due to the individual signal contributions, noise and interference from alloy microstructural features such as grain size, grain boundaries, carbide precipitates, inclusions and dislocations. While Moorthy found that variation in carbon content at various depths significantly influences MBN levels, due to the extensive carbide precipitation created by carbon diffusion into alloy samples and the dominance of the mean critical fields produced by these precipitates, Moorthy found that the MBN technique was better suited to measurement of hardness profiles in processed alloys.

Ultrasonic techniques for measuring alloy microstructural features such as case hardness depth have been evaluated by a number of workers [see B. R. Tittman, "Determination of Physical Property Gradients from Measured Surface Wave Dispersion." *IEEE Transactions on Ultrasonics, Ferroelectrics, and Frequency Control*. September 1987, p. 500–507; B. R. Tittman, et al., "Measurement of Physical Property Gradients with Elastic Surface Wave Dispersion." *Proceedings of the 9$^{th}$ Symposium on NDE*. Apr. 25–27, 1973, p. 20–28; C. W. Richards, *Engineering Materials Science*. 6th printing. Wadsworth Publishing Company, Inc., 1968; N. Borzorg-Grayeli, "Acoustic Nondestructive Evaluation of Microstructure." Ph.D. Thesis, Stanford University, 1981; M. Pancholy, et al., "Ultrasonic Attenuation in Carbon Steels." *Indian Journal of Technology*. 19(12):493–498 (1981); A. Idris, et al., "Acoustic Wave: Measurements at Elevated Temperature Using Pulsed Laser Generator and an Electromagnetic Acoustic Transducer Detector." *Nondestructive Testing and Evaluation*. Vol. 11. No. 4. 1994, p. 195–213; D. R. Mitra "Case Depth Evaluation of Carburized Specimens Using Ultrasonic Methods." B. S. and M. Sc. Thesis, MIT, 1993]. Such methods are rather limited for carbon profile measurements in steels due to the significant ultrasonic scattering and attenuation observed with austenitic structures and the anisotropic properties in heat treated alloys [see M. Pancholy, et al., *Indian Journal of Technology*. 19(12):493–498 (1981)]. Perhaps the most successful of these acoustical methods was that of Mitra who employed both contact transducers and non-contact, electromagnetic acoustic transducers (EMAT) to measure Raleigh wave velocities at varying frequencies in case hardened alloy samples. While Mitra was able to accurately correlate measured Raleigh wave velocities with case depth at low frequencies with his EMAT method, the technique could not provide reliable measurements of carbon concentration profiles.

Due to the limitations of such conventional carbon sensors and sensing methods for accurately determining carbon concentration profiles in carburized alloys at temperature during carburizing heat treatments, there is a pressing need to develop a reliable, real-time, direct measurement device and method for accurate measurement and control of carbon concentration profiles during carburizing heat treatments of alloy materials. Such a device, when employed with a properly designed process control system could significantly reduce or eliminate problems with over carburization in current commercial processes and provide a substantial cost savings for the heat treating industry.

It would be particularly advantageous if a measurement device, system and method were available which could directly measure a physical property profile which is created by a carbon gradient to provide measurement of carbon concentration profiles in carburized alloys during processing. Thus, a carbon sensor probe, measurement system and measurement method of the present invention, which employs electrical resistivity profile measurements for determining carbon concentration profiles in processed alloys during processing, appear to offer a heretofore unrecognized, unappreciated and unrealized solution to non-destructive, direct, real-time carbon profile measurements of processed alloys.

SUMMARY OF THE INVENTION

The present invention relates to a resistivity profile probe, an alloy solute concentration depth profile sensor probe, an alloy solute concentration depth profile sensing system and non-destructive method for directly measuring alloy solute concentration profiles in real-time at elevated process operating temperatures. The alloy solute sensor probe, sensing system and sensing method of the present invention exploit the combined interaction and synergy of two distinct and diverse DC and AC electrical phenomena observed in conductive materials: a) the observed variation in DC electrical resistivity due to additions of small amounts of elemental impurities in conductors; and b) the observed variation in AC current flow with depth in conductors due to variation in frequency. The ability to sample a series of defined alloy subsurface volumes at varying depths and determine the incremental resistivity of each of the sampled volumes with the sensor probe, sensing system and sensing method of the present invention enable the direct, real-time, non-destructive measurement of alloy solute concentration profiles in alloys at elevated processing temperatures.

The method and device of the present invention advantageously exploit the observed electrical behavior of conductive alloys whereby, by passing alternating current through a conductor over a range of frequencies and measuring the conductor resistance at each frequency, a resistivity depth profile within the conductor may be measured. For conductors having uniform composition, the resistivity is typically uniformly uniform throughout the sampled volume. However, when elemental impurities are introduced at the surface of a conductor and a compositional gradient is created which extends from the surface to the interior, the presence of the impurity concentration gradient will create a corresponding gradient in conductor resistivity. Thus, the principal objective of the present invention, to provide a device and method which can directly measure electrical resistivity profiles created in conductors due to elemental compositional gradients, enables the direct measurement of elemental concentration profiles in such alloys. While the capabilities and advantages of the present invention have been demonstrated through measurement of carbon concentration profiles in steel alloys, the disclosed device and method may be appropriately modified by one skilled in the art to measure compositional gradients of other solute elements in a variety of conductor materials where conductor resistivity varies in a predictable manner with solute concentration.

In one disclosed embodiment of the non-destructive, direct, real-time solute concentration gradient sensor, sensing method and system, a concentric carbon sensor probe is provided for measuring in-depth carbon concentrations in alloys at elevated processing temperatures. The concentric carbon sensor is brought into contact with an alloy part that is being carburized and nondestructively profiles the subsurface alloy carbon concentration in real-time during processing. In an alternative disclosed embodiment, a separate, stand-alone carbon sensor is provided for independently measuring carbon profiles without requiring actual contact with alloy components. The stand-alone sensor comprises an alloy test rod that may be located in the vicinity of the processed alloy part. Both sensor embodiments rely on electrical skin effect phenomenon and the solute concentration dependence of resistivity for measurement and mapping of carbon profile measurements. Both probe embodiments comprise simple mechanical designs which provide high electrical and mechanical reliability and repeatability.

One object of the present invention is to provide an alloy solute sensor probe for sequestering and sampling a plurality of defined subsurface volume elements of a conductive material or alloy and measuring both the subsurface concentration of a solute in each of said defined sample volume elements as well as the subsurface concentration profile of a solute at an external surface of the material. The sensor probe comprises: a) a first electrode in contact with a first portion of an external surface of said conductive alloy, said first electrode defining a first boundary surface of each of said sample volume elements; b) a second opposing electrode in contact with a second portion of said external surface, said second electrode defining a second boundary surface of each of said volume elements; and c) a variable frequency alternating current source attached to said first and second electrodes, wherein said current source provides a plurality of alternating current frequencies to said first and second electrodes, where each frequency f of said current source defines a third boundary surface of each of said volume elements at a subsurface depth δ defined as $$\delta = \frac{1}{\sqrt{\mu\sigma\pi f}}$$

where μ is the material magnetic permeability, σ is the material conductivity and f is the frequency of the applied AC current and where each of said volume elements is defined by the sampled material region enclosed by said first boundary surface, said second boundary surface, said third boundary surface and said external surface of said material.

A further object of the present invention is to provide a non-destructive, direct, real-time alloy solute sensor probe for profiling solute subsurface concentrations in conductive alloys.

Another object of the present invention is to provide a solute sensor probe which can sample a plurality of defined subsurface alloy volumes and measure the resistivity of each sampled volume over a range of sampling depths.

An additional object of the present invention is to provide a carbon sensor probe for measuring carbon concentrations and concentration profiles during carburization heat treatment of metal alloys.

Another object of the present invention is to provide an alloy solute sensor probe, sensing method and sensing system for control of thermal processing, doping and diffusion of solutes in alloys so as to produce preferred solute concentration profiles in alloy surface layers, for example case hardened surface layers created by carbon profiles in steel alloys.

A yet further object of the present invention is to provide a direct, real-time resistivity probe, control method and control system for induction heating and thermal processing of conductive materials.

An additional object of the present invention is to provide a resistivity probe, measurement method and measurement system for identification and measurement of fatigue surface cracks in conductive materials.

Despite the many advantageous features provided by conventional sensors for determining solute activity during alloy processing, it is anticipated that the solute sensor, sensing system and sensing methods of the present invention, which exploit the variation in alloy resistivity with solute content, may overcome the limitations of existing gas phase, electromagnetic and ultrasonic sensors, systems and methods by providing a direct, real-time measurement of solute concentration profiles in processed alloys at process operating temperatures. Furthermore, it is anticipated that the sensor, sensing system and sensing method as disclosed in the present invention can provide accurate control over thermal heat treatment processing so as to produce desirable solute profiles and treated alloy surfaces with greater precision at reduced cost. While examples are provided herein for carburization of steel alloys and measurement of carbon concentration profiles for case hardened surface layers, the device, process control system and method may be readily adapted to any industrial application where the heat treatment of alloy samples with desirable alloy solutes for the production of controlled surface compositional layers and properties is required. Furthermore, it is anticipated that the device, system and method of the present invention may be advantageously employed as an induction heating control system and for fatigue surface crack measurements.

BRIEF DESCRIPTION OF THE DRAWINGS

This invention is pointed out with particularity in the appended claims. Other features and benefits of the invention can be more clearly understood with reference to the specification and the accompanying drawings in which:

FIGS. 2A–2B show a schematic of electric field penetration in a metallic conductor (FIG. 2A) and the normalized magnitudes of the electric and magnetic fields as a function of depth (FIG. 2B);

DESCRIPTION OF THE PREFERRED EMBODIMENTS

The non-destructive, direct, real-time sensor device and method of the present invention relies on two diverse and unrelated electrical phenomena observed with conductor materials, Matthiesson's Rule [see A. Matthiessen et al., *Ann. d. Phys. U. Chem.* 122 (1864), p. 19–78; G. T. Meaden, "Conductivity, Electrical". *The Encyclopedia of Physics*. Editor Robert Besancon. $2^{nd}$ Ed. Van Nostrand Reinhold Company, New York, 1974. p 165; C. Kittel, C. *Solid States Physics*. 5th Ed., John Wiley & Sons, Reading, Mass., 1976. p 171; A. Decker, *Solid States Physics*. Prentice Hall Englewood Cliffs, N.J., 1957, p. 275 and 287; R. Bube, *Electron in Solids*. Academic Press, Inc., 1992, p. 178] and observations of frequency-dependant, alternating current flow behavior in conductor surfaces known as the "skin effect" [see W. Hayt Jr., *Engineering Electromagnetics*. McGraw-Hill (New York 1981), p 136; J. Jackson, *Classical Electrodynamics*. $2^{nd}$ Ed., John Wiley (New York, 1975); P. Clayton et al., *Introduction to Electromagnetic Fields*. $2^{nd}$ Ed., McGraw-Hill (New York 1987)].

1. Measurement Fundamentals

The carbon concentration profile measurement probe and method of the present invention rely on the synergy and combination of two distinct and unrelated electrical phenomena—the frequency dependence of alternating current flow in metallic conductors, known as the "skin effect", and observed variations in conductor resistivity due to the addition of small amounts of impurities on conductor resistivity, known as Matthiessen's Rule.

a. Matthiessen's Rule

Figure 1:
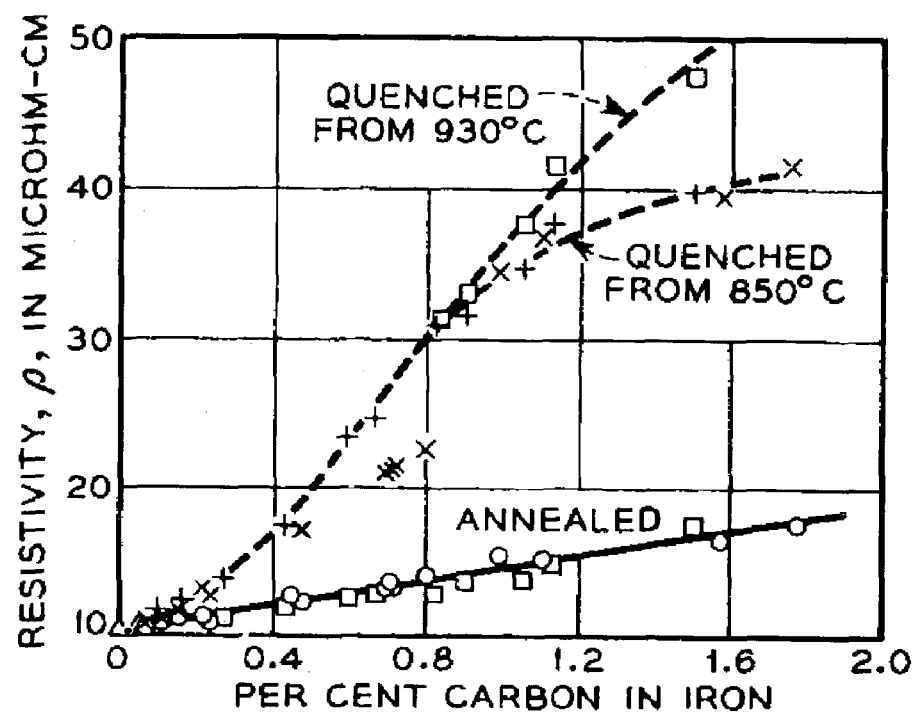
FIG. 1 is a plot of the variation in electrical resistivity with carbon concentration for iron-carbon alloys subjected to various heat treatments.

It is known in the art that the addition of certain solute elements produces a measurable, temperature-independent change in the electrical resistivity of alloys [see A. Matthiessen et al., *Ann. d. Phys. U. Chem.* 122 (1864), p. 19–78; M. R. Bozorth, *Ferromagnetism*, $6^{th}$ ed., Van Nostrand, (Princeton, N.J.) 1951, p. 6, 367, 716]. Matthiessen's rule states that the effect of adding small amounts of impurities to metals is that of adding a temperature-independent contribution to the resistivity. Thus if $\rho_{Th}$ is the thermal resistivity, and $\rho_o$ is the impurity contribution to resistivity, then the total resistivity is, $\rho=\rho_{Th}+\rho_o$. Studies by Gumlich and Campbell on carbon steels at room temperature have shown the dependence of electrical resistivity on percentage carbon and on heat treatment [see M. R. Bozorth, *Ferromagnetism*, $6^{th}$ ed., Van Nostrand, (Princeton, N.J.) 1951, p. 6, 367, 716; E.D. Campbell et al., "The Specific Resistance and Thermo-Electromotive Potential of Some Steels Differing Only in Carbon Content", *J. Iron and Steel Inst.*, vol. 63(1): 375–392 (1926)]. Their data are summarized and graphed by Bozorth (see FIG. 1). As shown in FIG. 1, the observed increase in electrical resistivity with increasing carbon content appears to confirm Matthiessen's Rule behavior with carbon in steel. According to Matthiessen's rule, if the resistivities of different layers in an alloy sample can be measured, then the measured resistivity should equal the sum of the resistivity due to lattice scattering and the resistivity due to carbon impurities. At a fixed temperature, the difference in resistivity between two different layers in an alloy should provide a measure of the difference in carbon content between the two layers.

b. Skin Effect

In order to appreciate the advantageous features and measurement basis for the sensor probe of the present invention it is necessary to consider the frequency-dependent characteristics of AC current flow in conductors and the resultant frequency-dependent skin effect [see W. Hayt Jr., *Engineering Electromagnetics*. McGraw-Hill (New York 1981), p136; J. Jackson, *Classical Electrodynamics*. $2^{nd}$ Ed., John Wiley (New York, 1975); P. Clayton et al., *Introduction to Electromagnetic Fields*. 2nd Ed., McGraw-Hill (New York 1987].

The frequency dependence of AC current flow and skin depth effects may be rationalized if one considers Maxwell's equations in point form in a region free of charge, $$\nabla \times E = -\mu \frac{\partial H}{\partial t} \quad (1.1)$$

$$\nabla \times H = -\sigma E + \varepsilon \frac{\partial E}{\partial t} \quad (1.2)$$

$$\nabla \cdot E = 0 \quad (1.3)$$

$$\nabla \cdot H = 0 \quad (1.4)$$

along with their constitutive equations, $J = \sigma E$, $D = \varepsilon E$, and $B = \mu H$.

In order to develop an expression for the constant of propagation, and for the wave equation, a separation of the electric field vector E and magnetic field vector H is necessary. Consider the curl of equation (2.1) and substitutes this in equation (2.2), using the vector identity, $\nabla \times \nabla \times V = \nabla(\nabla \cdot V) - \nabla^2 V$ where $\nabla^2 V$ is the vector Laplacian described as, $$\nabla^2 V = \nabla^2 V_x a_x + \nabla^2 V_y a_y + \nabla^2 V_z a_z$$
$$= \left(\frac{\partial^2 V_x}{\partial x^2} + \frac{\partial^2 V_x}{\partial y^2} + \frac{\partial^2 V_x}{\partial z^2}\right)a_x + \left(\frac{\partial^2 V_y}{\partial x^2} + \frac{\partial^2 V_y}{\partial y^2} + \frac{\partial^2 V_y}{\partial z^2}\right)a_y +$$
$$\left(\frac{\partial^2 V_z}{\partial x^2} + \frac{\partial^2 V_z}{\partial y^2} + \frac{\partial^2 V_z}{\partial z^2}\right)a_z$$

Similarly, if one takes the curl of equation (1.2) and substitutes this in equation (1.1) one obtains $$\nabla \times \nabla \times E = \nabla \times \left(-\mu \frac{\partial H}{\partial t}\right) \quad (1.5)$$
$$= -\mu \nabla \times \left(\sigma E + \varepsilon \frac{\partial E}{\partial t}\right)$$
$$= -\mu \sigma \frac{\partial E}{\partial t} - \mu \varepsilon \frac{\partial^2 E}{\partial t^2}$$

$$\nabla \times \nabla \times H = \nabla \times \left(\sigma E + \varepsilon \frac{\partial E}{\partial t}\right) \quad (1.6)$$
$$= -\mu \sigma \frac{\partial H}{\partial t} - \mu \varepsilon \frac{\partial^2 H}{\partial t^2}$$

Using equations (1.3) and (1.4) and substituting the vector Laplacian into equations (1.5) and (1.6) one obtains $$\nabla^2 E = \mu \sigma \frac{\partial E}{\partial t} + \mu \varepsilon \frac{\partial^2 E}{\partial t^2} \quad (1.7a)$$

$$\nabla^2 H = \mu \sigma \frac{\partial H}{\partial t} + \mu \varepsilon \frac{\partial^2 H}{\partial t^2} \quad (1.7b)$$

The vector differential equations shown in equations (1.7a) and (1.7b) are known as the wave equations or Helmholtz equations.

If the fields are expressed in phasor forms, $E(t) = E_0 e^{j\omega t}$, then the partial derivative operator, $$\frac{\partial()}{\partial t},$$

may be replaced by the factor $j\omega$. Thus equations (1.7a) and (1.7b) become $$\nabla^2 E = j\omega\mu(\sigma + j\omega\varepsilon)E \quad (1.8a)$$

$$\nabla^2 H = j\omega\mu(\sigma + j\omega\varepsilon)E \quad (1.8b)$$

If we designate the new parameter, $\gamma$, such that $\gamma^2 = j\omega\mu(\sigma + j\omega\varepsilon)$, we obtain $$\nabla^2 E = \gamma^2 E$$

$$\nabla^2 H = \gamma^2 H$$

The parameter $\gamma = \sqrt{j\omega\mu(\sigma + j\omega\varepsilon)}$ is known as the "propagation constant." Note that $\gamma^2$ as well as $\gamma$ are complex. Therefore, $\gamma$ may be expressed in terms of its real component and its imaginary component such that $\gamma = \alpha + j\beta$. The quantity $\alpha$ is called the attenuation constant, and the quantity $\beta$ is called the phase constant.

$$\gamma = \sqrt{j\omega\mu(\sigma + j\omega\varepsilon)}$$
$$= j\omega\sqrt{\mu\varepsilon}\sqrt{1 - j\frac{\sigma}{\omega\varepsilon}}$$

The ratio $$\frac{\sigma}{\omega\varepsilon}$$

is commonly called "the loss tangent." For a metallic conductor, for example metal alloys such as steel, and in the range of frequencies of interest (below 110 MHz), it is safe to assume that $$\frac{\sigma}{\omega\varepsilon} \gg 1;$$

hence the expression for the propagation constant reduces to $$\gamma = j\omega\sqrt{\mu\varepsilon}\sqrt{-j\frac{\sigma}{\omega\varepsilon}}$$
$$= \sqrt{j}\sqrt{\mu\sigma\omega}$$

Note that $$\sqrt{j} = \frac{1}{\sqrt{2}} + j\frac{1}{\sqrt{2}}$$

and $\omega = 2\pi f$

It follows that $$\gamma = \sqrt{\mu\sigma\pi f} + j\sqrt{\mu\sigma\pi f}$$

Therefore, in the metallic conductor case, the attenuation constant and the phase constant are $$\alpha = \beta = \sqrt{\mu\sigma\pi f} \quad (1.9)$$

Expanding Eq. 1.8a in terms of components using the vector Laplacian, the wave equation for phasor components of the field vectors becomes $$\gamma^2 E_x = \frac{\partial^2 E_x}{\partial x^2} + \frac{\partial^2 E_x}{\partial y^2} + \frac{\partial^2 E_x}{\partial z^2}$$

$$\gamma^2 E_y = \frac{\partial^2 E_y}{\partial x^2} + \frac{\partial^2 E_y}{\partial y^2} + \frac{\partial^2 E_y}{\partial z^2}$$

$$\gamma^2 E_z = \frac{\partial^2 E_z}{\partial x^2} + \frac{\partial^2 E_z}{\partial y^2} + \frac{\partial^2 E_z}{\partial z^2}$$

A similar set of wave equations may be obtained for the H-field.

In order to pursue mathematical treatments of the skin effect, it is essential to illustrate the significance of the propagation constant, $\gamma$. Without loss of generality, consider a uniform plane-wave whose electric E and magnetic H fields are orthogonal and always in a plane perpendicular to the direction of wave propagation. For illustration purposes, assume that the electric field E has only an x-component that varies with z, such that $E = E_x(z)$, and that the magnetic field H has only a y-component that varies with z, such that $H = H_y(z)$. Thus, the set of wave equations provided above are simplified to yield the following differential equations, $$\gamma^2 E_x = \frac{\partial^2 E_x}{\partial z^2} \quad (1.10)$$

$$\gamma^2 H_y = \frac{\partial^2 H_y}{\partial z^2} \quad (1.11)$$

Each of the equations (1.10) and (1.11) have two independent solutions. Only the ones associated with a forward traveling wave will be considered, namely, $$Ex = E_{x0}e^{-\gamma z} \text{ and } Hy = H_{y0}e^{-\gamma z} \quad (1.12)$$

where $E_{x0}$ and $H_{y0}$ are the magnitudes of the fields just at the surface. Substituting the relationship $\gamma = \alpha + j\beta$ into equation (1.12) yields $$E_x = E_{x0}e^{-\alpha z}e^{-j\beta z} \text{ and } H_y = H_{y0}e^{-\alpha z}e^{-j\beta z}$$

The effect of $\alpha$ and $\beta$ is that for a wave whose electric and magnetic fields are E and H respectively, as the wave travels in the conductor a distance of z, the fields will be attenuated by $e^{-\alpha z}$ in magnitude, and phase shifted by $-\beta z$.

The electric field of the assumed plane wave may be expressed as $E = E_x a_z$, where $E_x = E_{x0} \cos(\omega t)$. If this plane wave enters the surface of a sheet of a metallic conductor, for example a metal alloy such as a steel, the amplitude and phase of the plane wave inside the steel will be $$E_x = E_{x0}e^{-\alpha z}\cos(\omega t - z\beta) \quad (1.13)$$

$$= E_{x0}e^{-z\sqrt{\mu\sigma\pi f}}\cos(\omega t - z\sqrt{\mu\sigma\pi f})$$

Consequently, the current density, $J = \sigma E$ becomes $$J_x = \sigma E_{x0}e^{-z\sqrt{\mu\sigma\pi f}}\cos(\omega t - z\sqrt{\mu\sigma\pi f}) \quad (1.14)$$

In terms of magnitude, it is clear from the above equations (1.13) and (1.14) that as we move away from the source at the surface, the electric field as well as the current density decay with increasing depth z. This is shown schematically in FIGS. 2A and 2B where the magnitude of the electric field decreases with increasing depth. This decay is a function of the depth z, the conductivity of the metal, and the frequency of the excitation signal—the current is confined to the surface layer or the skin of the metal. To illustrate, consider the special cases of depths of Table 1.

TABLE 1

Magnitudes Of The Fields Or Current Densities At Special Depth Values.

| | | |
|---|---|---|
| At z ≈ 0, almost zero depth, or just at the surface | $\|E\| = E_{x0}$, maximum amplitude | $\|J\| = \sigma E_{x0}$ $= \|J_0\|$ |
| At z → ∞ | $\|E\| = 0$, total attenuation | $\|J\| = 0$, total attenuation |
| At $z = \frac{1}{\sqrt{\mu\sigma\pi f}}$, Or one skin depth | $\|E\| = E_{x0}e^{-1}$, amplitude attenuation by about 64 percent, and power attenuation by 86.5 percent | $\|J\| = \|J_0\| e^{-1}$ attenuation by about 64 |

In considering equation 1.14, it is common to express the current and field penetration into the metal in terms of a characteristic quantity, $\delta$, known as the "skin depth" of the material where $$\delta = \frac{1}{\sqrt{\mu\sigma\pi f}} \quad (1.15)$$

The critical depth into the metal, $z = \delta$, is the depth at which the amplitude of the field and the current density attenuate by a factor of 1/e from their value at the surface. The value of the skin depth, $\delta$, is a measure of the depth to which an electromagnetic wave can penetrate the metallic conductor. It is important to note that the skin depth decreases with increased frequency and is inversely proportional to the frequency of excitation.

FIG. 2A shows a schematic of the decreasing magnitude of the electric field penetration in a metallic conductor. FIG. 2B shows a plot of the normalized magnitude $E_x/E_{x0}$ (or $J_x/J_{x0}$ or $H_y/H_{y0}$) versus depth of penetration. At one skin depth ($z = \delta$), the field amplitude is about 37% of its surface value, at $3\delta$ the field is only 5% of its surface value. The power density is proportional to $(E_x)^2$, and thus the power density at one skin depth is only 13.533% of the surface power density. At three skin depths the power density is only 0.25% its value at the surface. For illustration, Table 2 shows different values of excitation frequencies and the corresponding skin depths in a typical slab of low carbon steel ($\sigma=0.5\times10^7 (\Omega m)^{-1}$ and $\mu_r=1000$ at room temperature [see *CRC Handbook of Chemistry and Physics*, 54$^{th}$ ed., R. C. Weast (Ed.), CRC Press (1973)].

TABLE 2

Example Skin Depth Penetration Into Steel At Room Temperature.

| Frequency (Hz) | $20 \times 10^6$ | $10^6$ | $10^5$ | $10^4$ | $10^3$ | $10^2$ | 10 | 1 |
|---|---|---|---|---|---|---|---|---|
| Skin depth (mm) | $0.05 \times 10^{-3}$ | $7 \times 10^{-3}$ | $2.2 \times 10^{-2}$ | 0.1 | 0.2 | 0.7 | 2.3 | 7.1 |

The electrical resistance of a conductive body depends on the electrical resistivity of the material, the material's geometry and dimensions, as well as the frequency of the current that is being pushed through the material. As shown in equation 1.14, due to the skin effect, at high AC frequencies the current density decays exponentially with depth as an electromagnetic wave attempts to penetrate the metal. Thus, only the skin portion of the conductor that has been penetrated by the current actually contributes to the resistance and the observed resistance is frequently referred to as the AC resistance, effective resistance or skin effect resistance of the conductor.

It has been previously demonstrated that, while the current flow surface region defined by the skin effect produced at a given frequency is bounded by an exponentially decaying surface, the skin effect resistance may be reasonably computed by assuming that the total current in the conductor is uniformly distributed over a thickness of one skin depth [see P. Rizzi, *Microwave Engineering*, Prentice-Hall, Inc., Englewood Cliffs, N.J., 1988; N. Rao, *Basic Electromagnetics with Applications*. Prentice-Hall, Inc. Englewood Cliffs, N.J., 1972; H. Skilling, *Electric Transmission Lines*, McGraw-Hill Book Co. New York, 1951]. This simplification of sequestered sample volume geometry, as provided by equation 1.15 and shown schematically in FIG. 5, greatly facilitates calculation of the resistance within the skin depth region at a given frequency and was employed with the device and method of the present invention for determining resistivity and solute concentration profiles in conductive alloys. As shown by Rizzi, Rao and Skilling, with this simplifying assumption the measurement of the resistance of the skin depth volume element is greatly facilitated by geometric simplification with negligible loss in measurement accuracy.

By way of example, consider the resistance of a round wire of radius a and length L. At high frequencies when the skin depth is much smaller than the radius a, ($\delta<<a$), the wire may be considered as a thin hollow conducting tube of length L, radius a and wall thickness $\delta$ and the AC current is considered to be uniformly distributed within the skin depth region. When applying the standard equation for wire resistance $$R = \rho \frac{L}{S}$$

where $\rho$ is the material electrical resistivity, L is the wire length, S is the skin depth cross-sectional surface area penetrated by the current, and assuming the current is uniformly distributed within the skin depth region of depth $\delta$, the AC resistance of the wire in ohms is given as $$R_{AC} = \rho \cdot \frac{L}{(2\pi a)\delta}.$$

Since the skin depth is inversely proportional to the frequency of the AC current according to equation 1.15, as the frequency f decreases, the skin depth $\delta$ increases and the AC resistance $R_{AC}$ decreases. Where the applied current is DC or a low frequency AC current such that $\delta \approx a$, the entire circular cross-sectional area of the wire is penetrated by the current, and the resistance in ohms is given as $$R_{DC} = \rho \cdot \frac{L}{\pi a^2}.$$

2. Probe Design

One of the key features of the sensor probe design and measurement method of the present invention is the ability to sequester and sample a specified conductive alloy volume element which is defined by the geometry of the two electrodes and the conductor skin depth $\delta$ which is established by the frequency of the applied AC current. In Section A details of a concentric electrode sensor probe of the present invention are provided. In Section B details of a rod-type sensor probe of the present invention are presented.

A. Concentric Electrode Probe

Section 1 provides details of the concentric sensor probe design, geometry and field characteristics. Section 2 provides the theoretical basis and mathematical relationships employed for measuring subsurface resistance and for deriving resistivity profiles with the concentric sensor probe of the present invention. Section 3 provides experimental configurations and procedures used for demonstrating the concentric probe design concept and measurement capabilities over a range of frequencies.

1. Concentric Probe Design Considerations

Figure 8A:
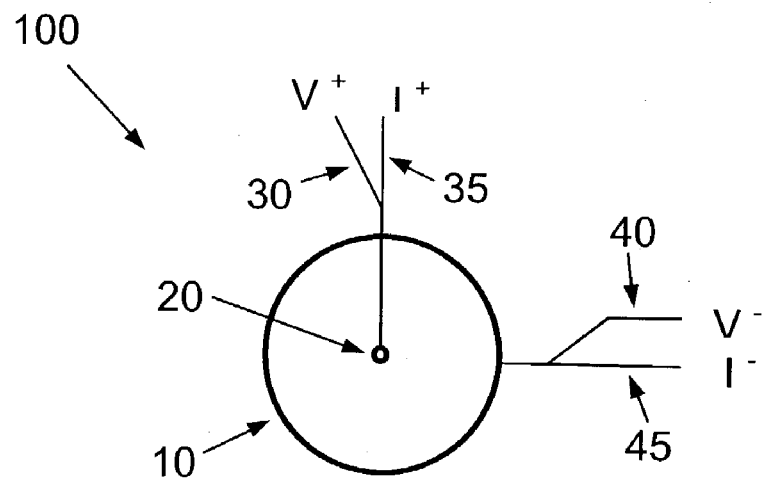
FIGS. 8A–8B show a schematic of one embodiment of a four wire concentric probe connection (FIG. 8A) and an improved four wire connection embodiment (FIG. 8B) respectively.
Figure 8B:
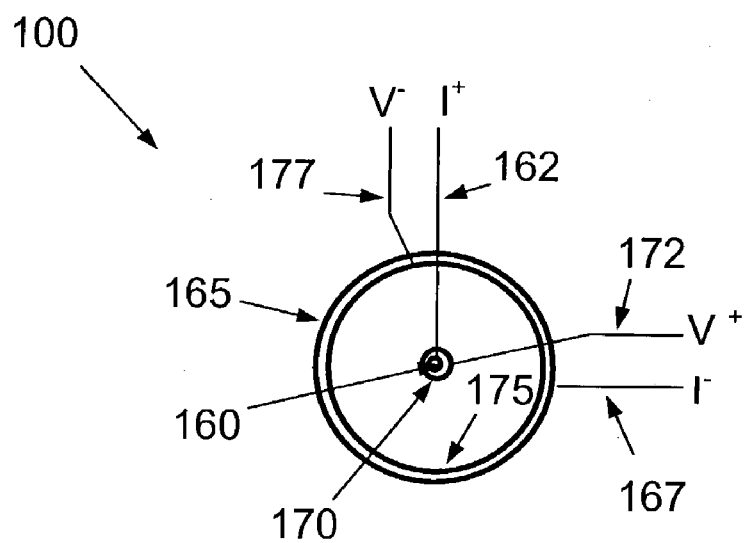

For measurement of sample AC resistance and determination of resistivity, the concentric probe geometry generally comprises a four wire ohm meter connection, with two voltage and two current leads, to either two or four concentric electrode conductors mounted in the same plane as shown in FIG. 8A for a two electrode probe and in FIG. 8B for a four electrode probe. In the embodiment shown in FIG. 8A, a voltage 30, 40 and current 35, 45 lead are connected to each of the two concentric electrode conductors 10, 20 which are employed as electrodes. In this embodiment the effect of the four lead contact resistance is eliminated but the contact resistance of the current source connection is not completely eliminated. In a preferred alternative embodiment shown in FIG. 8B, either a voltage 172, 177 or a current 162, 167 lead are connected to each one of four concentric electrode conductors 160, 170, 165, 175. This configuration is employed to eliminate the effects of both lead contact resistance and current source contact resistance.

In order to demonstrate the advantageous design feature of the concentric probe of the current invention, measurements of DC voltage and mapping of AC simulated voltage fields was conducted. In these simulation measurements, the electrode configuration shown in FIGS. 4 and 8A and experimental configuration shown in FIG. 3 were employed and an analog field plotter (not shown) was used to measure the field maps. The field maps were utilized to demonstrate the unique capability of the concentric probe for sequestering of a defined sample volume element, bounded by the equipotential boundaries formed by the inner 20 and outer 10 electrodes and frequency dependent skin depth δ (see equation 1.15) for the purpose of measuring subsurface conductor resistance profiles. In addition, the field maps demonstrate the basis for formulation and derivation of the resistance and resistivity equations for the conductor volume element sequestered by the probe. The analytical basis and resultant equations for resistance and resistivity measurements are provided below.

Figure 3:
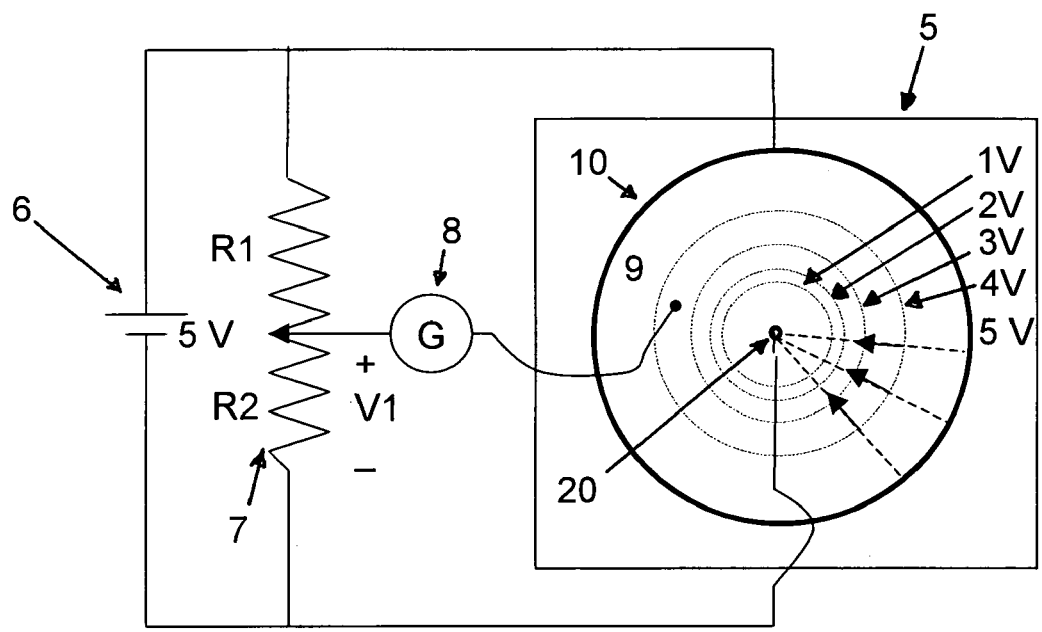
FIG. 3 is a schematic diagram of an experimental positive half cycle electric field mapping showing isopotential and flux lines for a concentric probe of the present invention.

A two-dimensional field map of the carbon probe consists of a set of equipotential lines representing the voltage distribution and a set of electric force or flux lines representing the electric field distribution (see FIG. 3). The equipotential lines represent lines of constant voltage potential which is the locus of all points to which a test charge may be moved without the exchange of energy. To move a test charge to a more positive or negative potential requires the expenditure of energy. Energy would be given off if a test charge were moved to a more negative or positive equipotential line. When a constant voltage is applied between the two electrodes 10, 20, a positive charge accumulates on one of the electrodes and an equal and opposite charge accumulates on the other. A typical voltage field map for a concentric electrode probe configuration of the present invention are shown in FIG. 3.

Several well-established characteristics of electrostatic fields are helpful in determining the field map and resultant flux lines. [see W. Hayt, Jr. *Engineering Electromagnetics*. McGraw-Hill Book Company, New York, 1981, p 136; S. Ramo et al., *Fields and Waves in Communication Electronics*. $2^{nd}$ ed., John Wiley (New York, 1984), p 148] They are as follows: a) As a consequence of filed boundary conditions, a conductor boundary is an equipotential surface; b) as a consequence of the electric field being the gradient of the voltage filed, $E=-\nabla V$, the flux lines are perpendicular to the equipotential lines; c) as a result of a) and b), the flux lines are perpendicular to the conductor surface; and d) the flux lines begin on the positive electrode and terminate on the negative electrode. Once the equipotential lines are determined experimentally, these properties can be applied to determine the flux lines. FIG. 3 shows a schematic of the configuration employed for measurement of equipotential lines with one embodiment of the concentric probe of the present invention.

In one two-dimensional hardware simulation configuration, shown schematically in FIG. 3, the two concentric electrodes 10, 20 of the carbon probe were placed in intimate contact with a flat resistive paper 5. The electrodes 10, 20 were made of silver paint whose electrical conductivity is significantly greater than that of the resistive paper 5. For these measurements, the radius of the inner electrode conductor 20 was 3 mm while the radius of the outer electrode conductor 10 was 65 mm. The electrodes 10, 20 were connected to the voltage source 6 and an analog field plotter (not shown) was used to measure and map the equipotential lines. The basic measurement system is the bridge circuit 7 shown in FIG. 3. The principle of operation is that when the bridge circuit 7 is balanced, the current through the galvanometer 8 is zero. Under this condition, the voltage $V_1$ is equal to the voltage $V_2$, where $V_1$ is found by the voltage divider principle, $$V_1 = V\left(\frac{R_2}{R_1 + R_2}\right)$$

As shown in FIG. 3, with the DC source set to +5 Volts, and the voltage $V_1$ adjusted to 1 Volt, the voltage probe 9 was moved around the resistive paper 5 to locate positions where the bridge circuit 7 was balanced. At each balanced point, $V_2$ must be equal to $V_1$, and the point must be on the contour of constant 1 Volt potential or the 1 Volt equipotential line. The coordinates of each point were recorded and a sufficient number of points were located and measured to construct a smooth equipotential curve. This curve was the contour of constant 1 Volt potential for the electrode 10, 20 configuration. Using polar coordinates, such that the origin coincides with the center of the inner conductor 20, it was found that all points defined by the locus of constant radius were equipotential points on the same equipotential circle. This procedure was repeated for $V_1=2$, 3, and 4 Volts. In Table 3, a summary of measurement results with the location of the equipotential curves for each voltage is provided. As shown in Table 3 and in FIG. 3, all the equipotential lines on the resistive paper 5 were found to be concentric circles lying between the inner 20 and outer 10 electrode

TABLE 3

Measured locations of equipotential contours.

| | |
|---|---|
| 0 Volt reference | Inner electrode boundary |
| +1 Volt equipotential contour | Circle whose radius is 5 mm |
| +2 Volt equipotential contour | Circle whose radius is 8 mm |
| +3 Volt equipotential contour | Circle whose radius is 17 mm |
| +4 Volt equipotential contour | Circle whose radius is 32 mm |
| +5 Volt equipotential contour | Circle whose radius is 65 mm (Outer electrode boundary.) |

Note: All points outside the outer electrode boundary were at a potential of +5 Volts.

conductors. It is important to note that no potential gradient was found outside the outer conductor 10 on the resistive paper 5.

The flux lines were plotted according to the properties outlined above and were found to be radial lines originating on the outer electrode 10 and terminating on the inner electrode 20. The existence of flux lines corresponds to the existence of the electric field. Alternatively, the absence of flux lines corresponds to the absence of the electric field. For illustration, three such flux lines are shown schematically in FIG. 3. It should be noted that while, from a practical point of view, a complete field map is unattainable, the experimentally generated map of FIG. 3 is of sufficient accuracy for design and engineering purposes.

These electric field measurements demonstrate that in the region located between the two concentric electrodes 10, 20 the electric field is not zero and outside the outer electrode 10 the electric field is zero. It is well established that the current density vector J is directly proportional to the electric field vector E where $J=\sigma E$, and the current I is directly proportional to the current density J where $I=A \cdot J$ and A is the cross-sectional area. From these relationships it can be established that there is no current flow in the zone outside the outer electrode 10 where $E=0$, and current exists only in the region between the two concentric electrodes 10, 20 where $E \neq 0$. Consequently, the resistance that the current encounters is only the resistance of the alloy material lying between the inner 20 and outer 10 electrodes.

In the hardware simulation and field mapping described above, a DC voltage source was employed and consequently only a static field map was generated. In order to simulate a probe field map for AC operation, the polarity of the electrodes was reversed and mapping was repeated. To establish a simulated experimental field map for an AC signal, one field map was generated for a positive half-cycle using the battery 6 polarity shown in FIG. 3 then another map was generated by manually reversing the polarity of the battery 6. This superposition is permissible because of the linear characteristic of resistance and the use of low AC signal frequency. With the DC source's polarities reversed, the field measurements were repeated and the electrostatic field was mapped. Mapping results are shown in Table 4 where measured equipotential contour radii for a simulated negative half cycle are provided.

TABLE 4

Measured locations of equipotential contours for a negative half cycle

| | |
|---|---|
| 0 Volt reference | Inner electrode boundary |
| −1 Volt equipotential contour | Circle whose radius is 5 mm |
| −2 Volt equipotential contour | Circle whose radius is 8 mm |
| −3 Volt equipotential contour | Circle whose radius is 17 mm |
| −4 Volt equipotential contour | Circle whose radius is 32 mm |
| −5 Volt equipotential contour | Circle whose radius is 65 mm (Outer electrode boundary) |

Note: All points outside the outer electrode boundary were at a potential of −5 Volts.

In comparing the results of Table 3 with those of Table 4, it is worth noting that the concentric equipotential lines shown in FIG. 3 have changed their polarities and the direction of the field has been reversed. These measurements demonstrated that no potential gradient and consequently no flux lines exist in the region located outside of the outer concentric electrode 10. An AC current signal connected across the electrodes of the probe will give rise to concentric equipotential lines whose magnitudes alternate back and forth. The AC signal also gives rise to an electric field that is in the radial direction, perpendicular to the electrodes 10, 20, and points radially outward or radially inward—depending on whether the positive half cycle or the negative half cycle is on.

Knowledge of the electric field map, combined with knowledge of frequency-dependent, skin depth current penetration behavior discussed above, enables application of AC current to the concentric probe electrodes for engaging and sequestering a defined, frequency-dependent, sample volume of conductive material, wherein a first boundary of the sample volume element is defined by the location of the inner electrode conductor, a second boundary of the sample volume element is defined by the radius of the outer electrode conductor, and the thickness or depth of the sequestered sample volume element is established by the application of AC current at a frequency which defines the "skin depth" $\delta$ (see equation 1.15) which is the approximate depth of current penetration into the alloy substrate material due to AC current skin effect phenomena. By providing for sampling a defined, frequency-dependent sample volume element, the sensor probe and method of the present invention enable measurement of the subsurface resistivity and resistivity profile of a conductive alloy sample at defined depths below the surface which, when combined with known resistivity variations due to alloy solutes, provide for measurement of subsurface alloy solute element concentrations and concentration profiles. The establishment of a defined, frequency-dependent sample volume during measurement and the measurement of the resistivity of a series of defined volumes at varying frequencies is unique to the sensor probe and method of the present invention and enables the determination of solute concentration profiles for a variety of alloys and alloy solutes, for example carbon in steel alloys.

2. Resistance and Resistivity Models

The general theoretical relationships and principles of operation for measurement of resistivity for the concentric sensor probe and rod-shaped sensor probe of the present invention are provided below. The derivation of the resistance equation is a modification of an analytical treatment for two dimensional DC electric fields provided by Bitter (see F. Bitter, *Currents, Fields, and Particles*, John Wiley (NY 1956) p.108–110.)

Consider the concentric probe described above and shown schematically in FIG. 4. Let $r_a$ and $r_b$ be the radii of the inner 20 and outer 10 electrode contacts. If an AC voltage $V_{ab}$ is applied across the concentric probe electrodes 10, 20 and the probe is placed in contact with a steel alloy sample plate, each of the concentric circular electrodes 10, 20 forms an equipotential ring and AC current flows in the radial direction through a sample volume element of finite thickness where the thickness is determined by current frequency according to the AC skin effect. The sequestered sample volume in which the electric field and current are active is shown schematically in FIG. 5 for three different applied frequencies where there the depth of current penetration increases with decreasing frequencies. The electronically sequestered sample volumes are approximated as cylindrical-shaped regions which share the same outer diameter as the concentric probe but whose depth or thickness varies with frequency such that greater penetration occurs at lower frequencies. It is important to note that FIG. 5 is for illustration purposes only and the drawing is not to scale. In FIG. 5 the depth of penetration $\delta$ is greatly exaggerated with respect to the radii $r_a$ and $r_b$ of the disk. As discussed above and shown in FIG. 5, the electric field has maximum strength at the surface of the steel. The magnitude of the electric field decays rapidly as the wave travels deeper into the steel. The depth of penetration z, normally expressed in skin depth units $\delta$, is inversely proportional to the frequency such that the higher the frequency the lesser the wave penetration.

The sample volume element, which is defined by the probe electrode geometry and applied frequency, is established for each applied frequency and enables the generation of in-depth resistivity and solute concentration profiles from measurements made over a range of appropriate frequencies. It is important to note that there is electrical resistance, as seen by the applied source, only in the region where the field and current have finite magnitudes where the flow of electronic charge is being impeded by the steel's resistance. Thus, the sample volume which is responsible for the measured resistance is the volume element sequestered by the field created by the applied AC current at a given frequency. For the purpose of analytical and geometric simplification, this volume element is approximated as an cylindrical-shaped volume with a radius $r_b$ and a depth or thickness z which is established at each applied current frequency and approximated by the skin depth $\delta$ at the applied frequency according to equation 1.15. As noted above, Rizzi and Rao have shown that this geometric approximation introduces negligible loss of accuracy in computation of the resistance of the sequestered sample volume element.

In preferred concentric electrode embodiments, the inner electrode conductor radius $r_a$ is typically very small, approaching a point and the effective volume radius is approximated as $r_b$. FIGS. 4A–C show three example sample volume elements whose three different thicknesses are established by varying AC frequencies to produce three different skin depths. It is important to note that in FIG. 5 the thickness of each alloy volume element relative to the respective probe diameter is not to scale and is exaggerated for the purposes of illustration.

For DC applications, where current flow is uniform throughout a conductor, the well known resistance equation for wires and bars applies, where ρ is the electrical $$R = \rho \frac{L}{S}$$

resistivity of the conductor, L is the length and S is the cross-sectional surface area [see R. Boylestad, *Introductory Circuit Analysis*. 8$^{th}$ Ed. Prentice Hall. Englewood Cliffs, N.J., 1997, p. 53–57; W. Callister, *Materials Science And Engineering: An Introduction*. 4$^{th}$ Ed. John Wiley & Sons, Inc. New York, 1997. p 592; W. Hayt, *Engineering Electromagnetics*. McGraw-Hill Book Company, New York, 1981, p 136; J. Krauss, *Electromagnetics*. McGraw-Hill, Inc. New York, 1992, p. 189]. However, for AC applications at high frequencies, current flow is non-uniform through conductors due to skin effect phenomena so the above equation does not apply.

For the purpose of deriving an equation for the total electrical resistance of a sequestered sample volume element at a given frequency, with the concentric probe and method of the present invention one must first consider a small differential volume element of steel situated at an arbitrary location between the inner and the outer electrodes and, within the small differential volume element, consider the current density J in amperes per unit area to be uniform. Then the differential currents are summed over a series of such elements over a concentric ring of arbitrary radius r to obtain the total current. Next, the differential voltage drops are summed over a series of such volume elements between the radii of the concentric conductors to obtain the total voltage. The resistance is then obtained by application of Ohm's Law. This procedure is explained in detail below.

Figure 4:
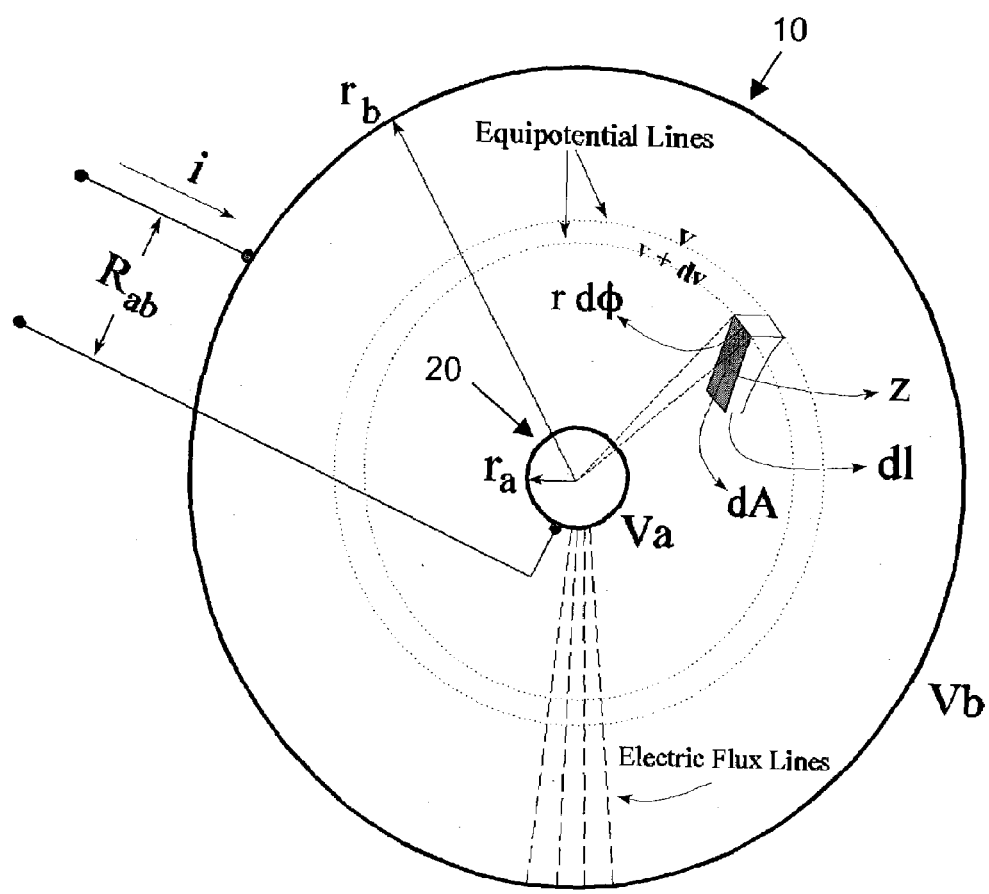
FIG. 4 shows a schematic diagram of the concentric probe in contact with an alloy sample with a differential volume element located between the inner and the outer electrodes of the probe at an arbitrary location.
Figure 5:
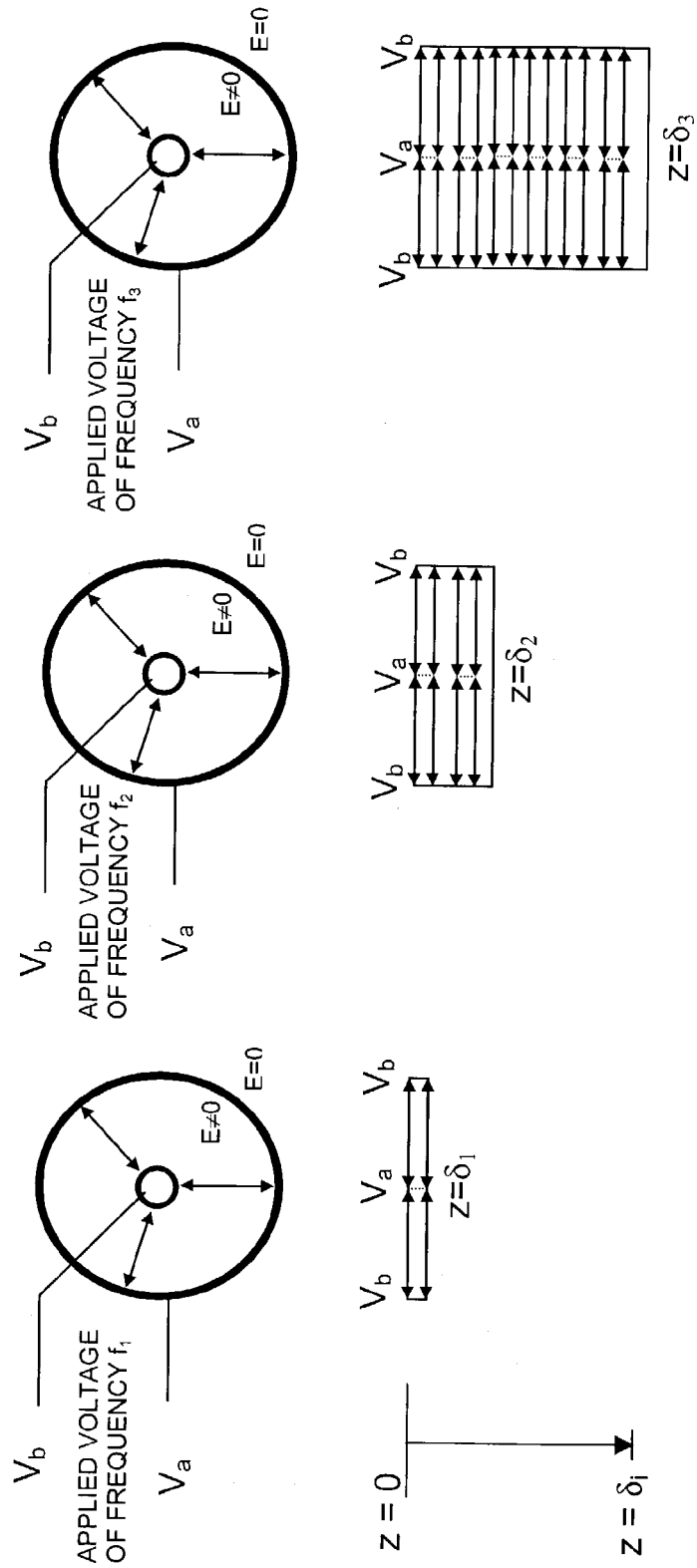
FIG. 5 shows schematic top views and cross-sections of three distinct sample volumes sequestered at frequencies $f_1>f_2>f_3$ with a concentric sensor probe where current penetration and sample volume depth increase with decreasing frequency.

Consider a differential rectangular volume element shown in FIG. 4 with length dl or dr and cross-sectional area dA, with current di flowing normal to a surface with area dA, and with a potential drop of dv across the differential volume element. One can apply Ohm's law in point form, where $J=\sigma \cdot E$, to the differential volume element, where J is the current density, σ is the conductivity, and E is the electric field. Substituting J=di/dA, σ=1/ρ, and E=dv/dl into J=σE and solving for dR=dv/di yields the resistance of the differential volume element, $$dR = \rho \frac{dl}{dA} \quad \text{or}$$
$$dR = \rho \frac{dr}{dA}$$

By Ohm's Law, dv=di dR or di=dv/dR, which yields, $$di = \frac{dv}{dR} = \frac{dv}{\rho \frac{dr}{dA}} \tag{1.16}$$

One can consider this isolated differential volume element applied to the concentric probe geometry of the present invention. In FIG. 4 a schematic of a concentric probe is shown in contact with and alloy sample with a differential volume element in an arbitrary location between the two electrodes 10, 20 in a region where the electric field is active or non-zero. The differential volume element can be employed for deriving the equation of total electrical resistance of the sampled volume of the alloy. In order to fully appreciate the derivation for the total resistance of a sampled alloy volume when employing the probe design of the present invention, there are a number of features worth noting regarding the probe configuration shown in FIG. 4:

a) The electrodes are held in intimate contact with an alloy component, for example a steel plate, which is to be tested. It is important to employ electrode materials whose conductivity is much higher than that of the alloy. For example, in preferred embodiments copper or platinum electrodes are employed. Where a multiple, repeated use sensor probe is required, a high electrical conductivity and heat resistant material such as platinum is preferred for enhance reliability and repeatability. Where inexpensive disposable sensor probes are desirable, copper electrodes may be employed. For the purpose of the analysis below, the two concentric electrodes are considered to be almost perfectly conducting rings of radii $r_a$ and $r_b$, the applied voltage between the electrodes is $V_{ab}=V_b-V_a$ and the inner and outer electrodes act as equipotential surfaces with voltages $V_a$ and $V_b$, respectively;

b) Based on the experimental electric field maps discussed above and the boundary conditions established by the interface between an excellent conductor and a poor conductor, it can be readily demonstrated that the electric flux lines are oriented in a radial direction and normal to the electrodes, beginning on one electrode and ending on the other and radiating either outward or inward, depending on whether the applied AC voltage is in a positive or negative half cycle. By way of illustration, in FIG. 4, four example flux lines are shown schematically as dashed lines. Current flow between the electrodes is in the same radial direction as the flux lines. This can be readily deduced from the point form of Ohm's law $J=\sigma \cdot E$ [see V. S. Marshall et al., *Electromagnetic Concepts and Applications*. 2$^{nd}$ ed. Prentice Hall (Englewood Cliffs, N.J. 1987) p. 114; S. Ramo, *Fields and Waves in Communication Electronics*. 2$^{nd}$ ed., John Wiley (New York 1984) p. 148];

c) The differential volume element shown in FIG. 4 is orientated such that the current density vector, which is in the radial direction, is normal to the differential increment of surface area dA;

d) In FIG. 4, two equipotential lines are shown schematically as concentric circular rings centered around the origin, as demonstrated experimentally in the measured experimental field maps shown in FIG. 3 and Tables 3 and 4. For illustration purposes, only two adjacent equipotential lines are shown as dotted circular lines in FIG. 4 and denoted by v+dv and v, where dv is the increment of electric potential and the voltage drop across the differential volume element;

e) The flux lines are always perpendicular to the equipotential lines since the electric field is the gradient of the voltage (E=−∇V); and f) For the purpose of clarity and to take advantage of the associated geometric symmetry, circular cylindrical coordinates with radius r, height z and azimuthal coordinate φ are used in the resistance derivation provided below.

The differential increment of surface area becomes dA=z r dφ, where z is the depth and rdφ is the width; r is an arbitrary radius. Substituting dA into di of equation 1.16 yields $$di = \frac{dv}{\rho \frac{dr}{dA}} = \frac{dv}{\rho \frac{dr}{zrd\varphi}} = \frac{\sigma dv z r}{dr} d\varphi \tag{1.17}$$

In FIG. 4, note that the current is the same at every point around a ring of radius r. Hence, the total current i through any ring-shaped section is $$i = \int di = \int_0^{2\pi} \left( \frac{\sigma dv z r}{dr} \right) d\phi$$

and hence $$i = \frac{2\pi \sigma z r}{dr} dv \tag{1.18}$$

Solving equation 1.18 for dv yields $$dv = \frac{i}{2\pi \sigma z} \frac{dr}{r} \text{ Volts} \tag{1.19}$$

Since dv is the voltage drop across the differential volume element, in order to obtain the total voltage drop between the two concentric electrodes, one must integrate equation 1.19 from inner electrode radius $r_a$, to outer electrode radius $r_b$.

$$v_{ab} = \int_{r=r_a}^{r=r_b} dv$$

$$v_{ab} = \int_{r_a}^{r_b} \frac{i}{2\pi \sigma z} \frac{dr}{r}$$

$$v_{ab} = \frac{i \ln\left(\frac{r_b}{r_a}\right)}{2\pi \sigma z}.$$

Using Ohm's law, $V_{ab} = i R_{ab}$, the expression for the resistance is given as $$R_{ab} = \frac{v_{ab}}{i} = \frac{\ln\left(\frac{r_b}{r_a}\right)}{2\pi \sigma z}$$

or $$R_{ab} = \rho \frac{\ln\left(\frac{r_b}{r_a}\right)}{2\pi z} \tag{1.20}$$

Note that ln($r_b/r_a$) is a dimensionless constant, ρ is in Ω.m, and z is in meters.

As shown by equation 1.20, the measured resistance is a function of probe geometry and dimensions (radii $r_a$ and $r_b$), resistivity of the sequestered steel, and depth of penetration by the field or current. For ease of measurement in the experimental portion of this work, the radius of the inner conductor $r_a$ was made extremely small compared to the radius of the outer conductor $r_b$. In one embodiment, the inner conductor was reduced to a fine point contact approximately 0.5 mm in diameter while the outer conductor had a diameter of approximately 16 cm.

One may use equation 1.20 and solve for the resistivity in Ohms-meters where $$\rho = \frac{2\pi R_{ab} z}{\ln\left(\frac{r_b}{r_a}\right)} \tag{1.21}$$

By combining equation 1.15 for skin depth with equation 1.20 and assuming z=δ, the frequency and resistance dependence of skin depth is given as $$\delta = \frac{2R}{f \mu_0 \mu_r \ln\left(\frac{r_b}{r_a}\right)}. \tag{1.22}$$

Although at low temperatures iron or steel alloys are ferromagnetic, ferromagnetism is destroyed at a Curie temperature of about 770° C. and they become paramagnetic [see W. Hayt Jr., *Engineering Electromagnetics*. McGraw-Hill 9New York 1981), p. 136; W. Hume-Rothery, W. *The Structures of Alloys of Iron*. Pergamon Press, (Oxford 1966); M. R. Bozorth, *Ferromagnetism*, 6$^{th}$ ed., Van Nostrand, (Princeton, N.J.) 1951, p. 6, 367, 716]. The typical range of carburizing temperatures is 760° C. to 1050° C., whereas the temperature most commonly used for carburizing is 925° C. [see *Carburizing and Carbonitriding*, American Society for Metals (Metals Park, Ohio) 1977]. At this temperature, steel is paramagnetic, and its magnetic permeability is close to that of free space where $\mu_r \approx 1$ and $\mu = \mu_0 \mu_r = 4\pi \times 10^{-7}$ (Hm$^{-1}$) [see C. W. Richards, *Engineering Materials Science*. 6th printing. Wadsworth Publishing Co., 1968; *CRC Handbook of Chemistry and Physics*, 54$^{th}$ ed., R. C. Weast (Ed.), CRC Press (1973)]. Hence, Equation 1.22 reduces to $$\delta = \frac{2R}{f \mu_0 \ln\left(\frac{r_b}{r_a}\right)} \tag{1.23}$$

Equations 1.21, and 1.23 are of great practical significance since equation 1.23 permits the computation of the skin depth using the measured AC resistance $R_{ab}$ of the sequestered steel, the frequency f of the AC test signal, and the probe's radial dimensions $r_a$ and $r_b$. Equation 1.21 permits the computation of the resistivity of the sequestered steel using the measured AC resistance, the skin depth, and the probe's dimensions.

3. Concentric Probe Experimental Procedures

Figure 7:
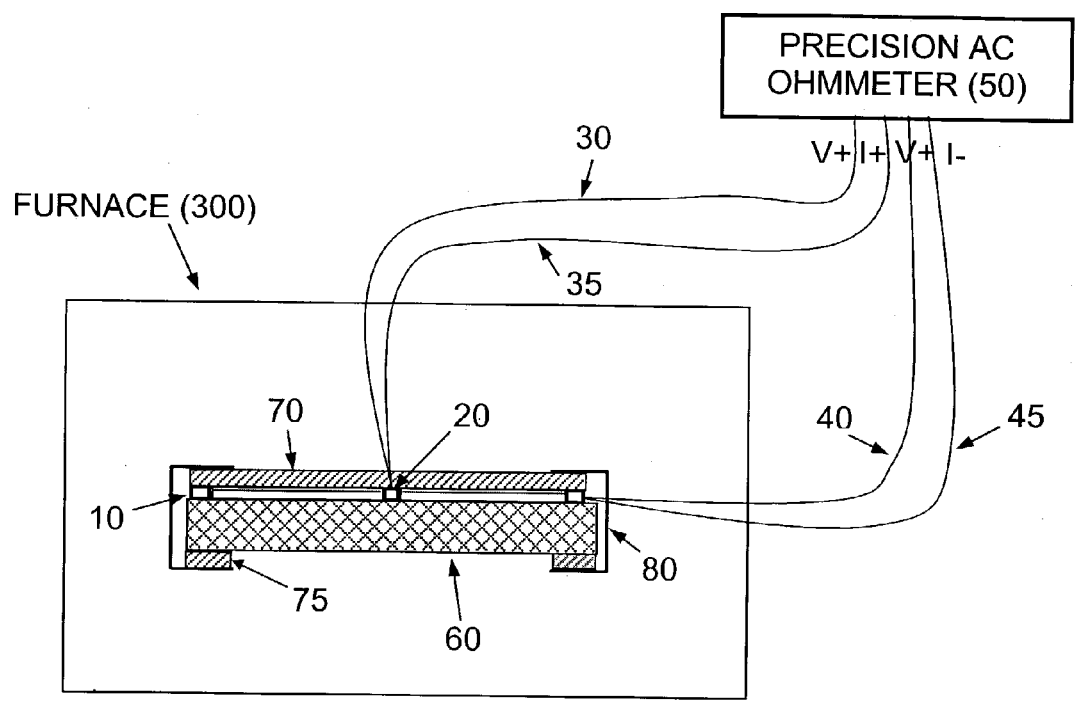
FIG. 7 is a schematic diagram of a typical experimental configuration used for carbon profile measurements using a concentric carbon probe of the present invention.

An experimental configuration employed for measuring AC resistance of carburized steel samples in the Austenite phase at 870° C. over a range of frequencies is shown in FIG. 7. Two concentric electrode embodiments are shown in FIG. 8A and FIG. 8B. The concentric electrode probes and measurement configurations as well as methods employed for measuring the resistivity profile at various depths away from the alloy sample surface and constructing a carbon depth profile from the resistivity profile are described below.

a. Experimental Configuration

In a preferred embodiment shown in FIG. 8A, a concentric outer electrode 10 and inner electrode 20 were fabricated from AWG#4 copper wire by cold forming a circular ring section on a cylindrical mandrel of a suitable diameter. Any excess wire was cut to form a tight joint where the wire ends of the ring meet and a wire lead was attached to the ring joint by cold forging. Alternatively, the ring ends and wire lead may be joined by either mechanical means, such as with conventional fasteners, or by welding or soldering with a suitable electrically conductive solder. In one preferred embodiment, a 16 cm diameter, outer concentric copper electrode 10 was employed. In an alternative preferred embodiment, a 13 cm diameter, outer concentric copper electrode 10 was employed. In one preferred embodiment, a center electrode 20 was formed from a 1 mm diameter copper wire. In an alternative preferred embodiment, a 0.5 mm diameter copper wire was employed as a center electrode 20. In one preferred embodiment, a 6 mm diameter copper wire was employed as a center electrode 20. In one preferred embodiment, a 16 cm diameter outer concentric copper electrode 10 was employed with a 1 mm diameter copper wire as a center electrode 20. In another preferred embodiment, a 0.5 mm diameter copper wire was employed as a center electrode 20 with a 16 cm diameter outer concentric copper electrode 10. In an alternative embodiment, a 6 mm diameter copper wire was employed as a center electrode 20 with a 13 cm diameter outer concentric copper electrode 10. Additionally, other embodiments with alternative in inner and outer concentric electrode dimensions are envisioned as being within the scope of the present invention providing that the ratio of the outer concentric electrode and inner electrode is sufficiently large to satisfy the analytical requirements noted below.

In the preferred embodiment shown in FIG. 8B, the concentric probe assembly 100 comprises four concentric electrodes with four lead wires, including a positive current electrode 160 and lead 162, a positive voltage electrode 170 and lead 172, a negative current electrode 165 and lead 167, and a negative voltage electrode 175 and lead 177. As discussed below, this four electrode, four wire configuration is preferred since it eliminates current lead contact resistance. As with the embodiment shown in FIG. 8A, the inner electrode 160 and the concentric electrodes 165, 170, 175 shown in FIG. 8B are fabricated from AWG#4 copper wires by cold forming a circular ring section on a cylindrical mandrel of a suitable diameter. Any excess wire was cut to form a tight joint where the wire ends of the ring meet and a wire lead was attached to the ring joint by cold forging. Alternatively, the ring ends and wire lead may be joined by either mechanical means, such as with conventional fasteners, or by welding or soldering with a suitable electrically conductive solder. In this embodiment, the positive current electrode 160 is connected to the current output of an AC precision ohmmeter 50 with wire lead 162 and the positive voltage electrode 170 is connected to the positive voltage terminal of the ohmmeter 50 with wire lead 172. In this embodiment, the negative current electrode 165 is connected to the negative current terminal of an AC precision ohmmeter 50 with wire lead 167 and the negative voltage electrode 175 is connected to the negative voltage terminal of the ohmmeter 50 with wire lead 177.

Alternative preferred embodiments may employ larger or smaller diameter wire and inner and outer electrode diameters. In addition, were measurements are to be made on very small component parts, miniature concentric electrodes which are made using conventional printed circuit board, semiconductor or microelectronic methods may be employed. For example conventional thick or thin film techniques may be employed for painting or coating concentric electrodes made from a conductive materials, such as copper, aluminum, gold or silver, on the surface of a component part.

In the concentric electrode probe examples provided herein, the inner electrode radii ranged from 0.25 mm to 3 mm, the outer electrode radii ranged from 6.5 cm to 14 cm and the ratio of the outer electrode radius $r_b$ to inner electrode radius $r_a$ ranged from about 21 to 320. It is important to note, however, that the concentric electrode probe of the present invention is not limited to these electrode dimensions. While the actual size of the inner and outer electrodes may be adapted to virtually any component size, in preferred embodiments, the inner electrode conductor radius $r_a$ is typically very small, approaching a point and the effective sequestered sample volume radius is approximated as the outer electrode radius $r_b$. As shown analytically above in equations 1.20, 1.21 and 1.23, for resistance, resistivity and skin depth measurements made with the concentric probe and measurement method of the present invention, it is preferable to maintain a large ratio of the outer to inner electrode radii where $r_b/r_a \gg 1$. If $r_b \cong r_a$, then $\ln(r_b/r_a) \cong 0$ such that the resistance $R \cong 0$, $\rho \cong \infty$ and $\delta \cong \infty$ and probe measurements will be prone to considerable measurement error.

While copper electrodes were employed for the measurements provided in Example 1–3 below, it is anticipated that other conductive materials such as copper alloys, platinum, gold, silver, aluminum metals and alloys and like metals having high electrical conductivity may be employed as electrodes so long as the conductors are stable at the measurement temperatures and do not react with the sample being measured or the surrounding atmosphere.

The concentric probe of the present invention may be readily configured for virtually any sample shape and dimension. In order to align the concentric outer electrode with the inner electrode and to provide for good contact with the sample which must be electrically insulated from any surrounding conductors, an electrically insulating clamping fixture may be employed. For example, FIG. 7 shows one embodiment of a clamping fixture used for the measurements presented in Example 2. In this embodiment, the concentric sensor probe 100 comprised an outer electrode 10, an inner electrode 20, a positive voltage lead wire 30, a positive current lead wire 35, a negative voltage lead wire 40 and a negative current lead wire 45 connected to a precision AC ohmmeter 50. The precision AC ohmmeters 50 s used for measurements described in Examples 1–3 were an Agilent technologies 4294A Precision Impedance Analyzer and Agilent Technologies 4285A and 4284A Precision LCR meters. The Agilent 4284A and Agilent 4285A AC ohmmeters have a measurement range of 0.01 mΩ to 99.99MΩ and a resolution of 10 μΩ.

As shown in FIG. 7, the inner 20 and outer 10 electrodes were aligned concentrically and held in place against the alloy sample 60 by a ceramic insulator plate 70. In order to position the two electrodes 10, 20 against the alloy 60, a shallow groove having the same diameter as the outer electrode 10 was machined in the bottom surface of the ceramic plate 70 and a small hole was drilled at the center of the machined groove to accommodate placement of the inner electrode 20. The plate 70 was clamped onto the top surface of the alloy sample 60 with a series of six C-clamps 80 which were electrically insulated from contact with the alloy sample 60 by ceramic insulator spacers 75. Virtually any electrically insulating material may be used for the insulator plate 70 and spacers 75 providing that the material does not react with the alloy or probe electrode materials and that it is thermally stable at anticipated measurement temperatures. For simplicity, only two C-clamps 80 are shown in FIG. 7. In order to make good electrical contact with the sample 60, in one embodiment the wire of the inner electrode 20 was bent to form a series of kinks or small spring coil so that the pressure of the top insulator plate 70 against the sample 60 compressed the electrode wire and urged the inner electrode against the alloy 60. Similarly, the pressure of the plate 70 against the sample 60 maintains the position of the outer electrode 10 relative to the inner electrode 20 and provides good electrical contact of the electrode 10 with the sample 60.

In the measurements presented in Example 2 below, a 2.54 cm thick alloy steel plate, having a 20.3 cm×20.3 cm area was employed for alloy sample 60 measurements. This sample 60 was a commercially available AISI 1018 steel that had been previously carburized and quenched at Lindberg Heat Treating Corporation (Worcester, Mass.). A Thermolyne-30400 furnace 300 was employed for heating samples and making measurements at carburizing temperatures.

For measurements made with both the concentric probe and rod-shaped probe which is discussed below, the precision ohmmeters 50 employed, namely the Agilent Technologies 4294A Precision Impedance Analyzer and the Agilent Technologies 4285A and 4284A Precision LCR meters, all utilized the same 4-lead Kelvin connection in a four terminal pair configuration. When switching from one meter to the other, only the BNC connection between the front-end panel of the Agilent instrument and the 4-lead Kelvin connectors set were switched. Thus, the measurement conditions, contact conditions and open/short compensation conditions were consistently maintained by leaving all other connections untouched.

In order to reduce measurement errors and achieve correct measurement of resistance, it was necessary to provide open-circuit and short-circuit compensation to eliminate the effect of residual and stray impedance. A calibrated substitution resistive wire was utilized in order to boost the reading well above the lower measurement range of the ohmmeters.

All electrode contact points and areas were cleaned to provide a smooth contact surface before use so as to minimize contact resistance. Sufficient mechanical pressure was exerted on the contact surfaces by means of the fixture and C-clamps shown in FIG. 7 so as to ensure minimal contact resistance. Since copper softens at the measurement temperature of 870° C, under the force of the C-clams, the electrodes were in intimate contact with the alloy sample during testing. Proper calibration of the meter was achieved by executing appropriate short circuit, open circuit, and leads' length compensation and corrections at temperature.

For carbon profile measurements, a previously carburized steel was reheated into the Austenite phase as the atmosphere temperature inside the furnace was raised to 870° C. This temperature was selected in order to provide measurements at a typical carburizing temperature and to ensure that the steel had become paramagnetic with a relative magnetic permeability of unity ($\mu_r=1$) regardless of the carbon gradient in the steel. The electric furnace was then turned off in order to eliminate internally generated interference and AC resistance measurements were rapidly taken and stored.

b. Resistance Measurements

Prior to determining the resistivity profile and concentration profile in a sample alloy, one must first measure the resistance of the alloy at various subsurface depths. In considering the following arrays, where R is the array of measured AC resistances, f is the array of test signal frequencies, δ is the array of depth of measurements into the steel and ρ is the array of resistivities, then $R_i$ is the measured AC resistance of the $i^{th}$ layer of steel, $\delta_i$ is the thickness of the $i^{th}$ layer which is the depth of penetration of the said AC signal at frequency $f_i$ where the thickness $\delta_i$ and the frequency $f_i$ are related by the skin depth equation 1.15. In making AC resistance measurements, as the frequency of the applied signal varies from $f_{i-1}$ to $f_i$, the skin depth also varies in accordance with the principles discussed above. Frequency $f_{i-1}$ produces a skin depth $\delta_{i-1}$ and frequency $f_i$ produces a skin depth $\delta_i$. The measured resistance $R_{i-1}$ is the total AC resistance of the sequestered steel measured at frequency $f_{i-1}$, and the measured resistance $R_i$ is the total AC resistance of the sequestered steel measured at frequency $f_i$. Decreasing the value of the frequency means that physically another layer of material, whose thickness is the difference between the two skin depths $|\delta_{i-1}-\delta_i|$, has been added in parallel with the layer whose resistance is $R_{i-1}$ to produce the total measured resistance $R_i$. as shown schematically in FIG. 6.

Figure 6:
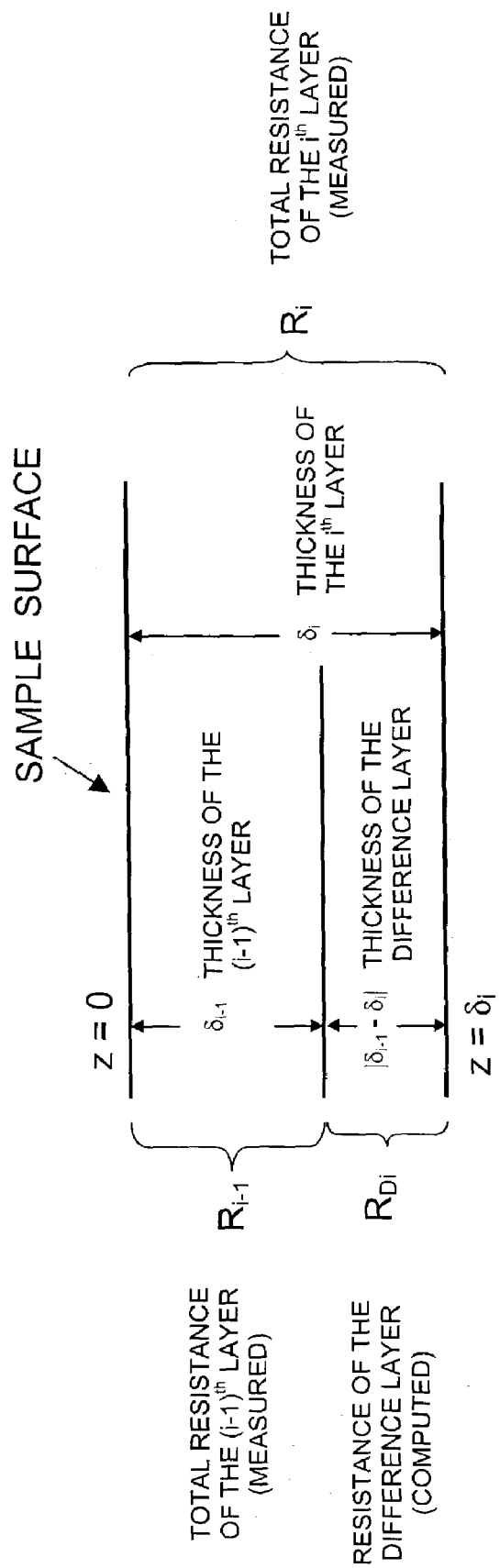
FIG. 6 is a two-dimensional schematic showing sequential subsurface sample volumes using the sample probe and solute profile measurement method of the present invention.

As shown schematically in FIG. 5 and FIG. 6, when the sample volume element sequestered by the sensor probe has the thickness $\delta_i$ and the total current flowing through the steel sample is I, due to the principle of conservation of charge and Kirchhoff's current law, the current I must be equal to the sum of the currents $I_{i-1}$ and $I_{di}$ flowing through the $(i-1)^{th}$ layer and the difference layer respectively, where the difference layer is the layer defined by $\delta_i-\delta_{i-1}$, such that $$I = I_{i-1} + I_{di} \quad (1.24)$$

If the AC voltage applied between the electrodes of the probe is $V_{ab}$, then one may consider that the voltage across the disks of material whose thickness $\delta_{i-1}$, and $\delta_i$ to be $V_{ab}$. Using Ohm's law, equation 1.24 may be rewritten as, $$\frac{V_{ab}}{R_i} = \frac{V_{ab}}{R_{i-1}} + \frac{V_{ab}}{R_{di}} \quad (1.25)$$

which yields, $$\frac{1}{R_i} = \frac{1}{R_{i-1}} + \frac{1}{R_{di}} \quad (1.26)$$

In equation 1.26, resistances $R_{i-1}$ and $R_i$ are known from measurements, and the only unknown is $R_{di}$, the resistance of the difference layer. Thus $$R_{di} = \frac{1}{\left[\frac{1}{R_i} + \frac{1}{R_{i-1}}\right]} \quad (1.27)$$

With $R_{di}$ determined, the average resistivity of the difference layer may be computed using equation 1.21 and the depth or location z of that layer is determined by first determining the values of $\delta_i$ or $\delta_{i-1}$ by using equation 1.23.

If intervals between test frequencies are selected to be small, then the resulting thickness of difference layer would be small compared to the depths $\delta_i$ or $\delta_{i-1}$. Therefore, the average resistivity of the difference layer $\rho_{di}$ is the resistivity at the difference layer depth $\delta_{di}$ given as $$\delta_{di} = \delta_i - \frac{|\delta_i - \delta_{i-1}|}{2}. \tag{1.28}$$

The resistivity value is then converted to corresponding percentage carbon weight using an empirically-derived calibration equation obtained from measurements of resistivities and carbon compositions made on actual alloy samples, for example, the following correlation between carbon composition and resistivity was derived from measurements made at 870 C. on an AISI 1095 steel alloy by the method disclosed in Example 1

$$\% \ C = 0.1818 \times 10^8 \rho - 21.1818 \tag{1.29}$$

where the resistivity $\rho$ is given in Ohms meter ($\Omega \cdot m$) and carbon composition is in weight percent. For other alloy compositions and solutes, alternative empirical correlations between alloy resistivity and solute concentration may be similarly derived from experimental measurements of solute concentrations and resistivities on a variety conductive alloy compositions using this approach.

With the precision ohmmeters employed in the measurements described in Examples 1–3, the instrumentation provides a variety of configurations for making resistance measurements with a fixed AC current, a fixed AC voltage or a variable AC current or AC voltage. Since four point resistance measurements are typically made with a fixed current, fixed current measurements were made for the data presented herein. In alternative embodiments either fixed voltage or variable current and voltage measurements may be employed. In preferred embodiments the current amplitude was set at a value sufficiently high so as to overcome signal noise but not so high as to saturate the measurement signal amplifiers. In typical measurements, instrument current was set at either 10 mA or 20 mA. With the precision ohmmeters employed in Examples 1–3, alternative instrument settings may be employed where the applied AC current or AC voltage is varied automatically so as to provide for a stable resistance measurement. Depending on the resistance value and stability of the measured signal, the precision ohmmeters may be configured for sample averaging of multiple measurements taken at a given sample rate. For the measurements provided in Examples 1–3 sample averaging of between 10 and 40 measurements was typically employed.

With the concentric sensor probe measurements provided in Example 2, a current frequency range of 45 kHz to 110 MHz was used. For the rod probe measurements provided in Examples 1 and 3, a current frequency range of 20 kHz to 4 MHz was employed. For most measurements, the minimum AC measurement frequency is the frequency where the skin depth $\delta$ of the alloy sample, as calculated using equation 1.15, is equal to or greater than the half thickness of the sample cross-section. This limiting frequency is where the measurement is equivalent to a DC measurement and current flows through the entire conductor volume. Since measurements of solute concentration profiles are the key objective of the device and method of the present invention, in preferred embodiments the minimum AC frequency is the frequency where the skin dept of the alloy is equal or slightly greater than the case depth or the depth to which the solute has penetrated into the alloy sample. As a limit to maximum frequencies, in preferred embodiments the maximum AC measurement frequency is the frequency where the skin depth $\delta$ of the alloy sample, as calculated using equation 1.15, provides acceptable in-depth spatial resolution for measurement of the resistivity and resultant solute concentration profile of the alloy.

Figure 9:
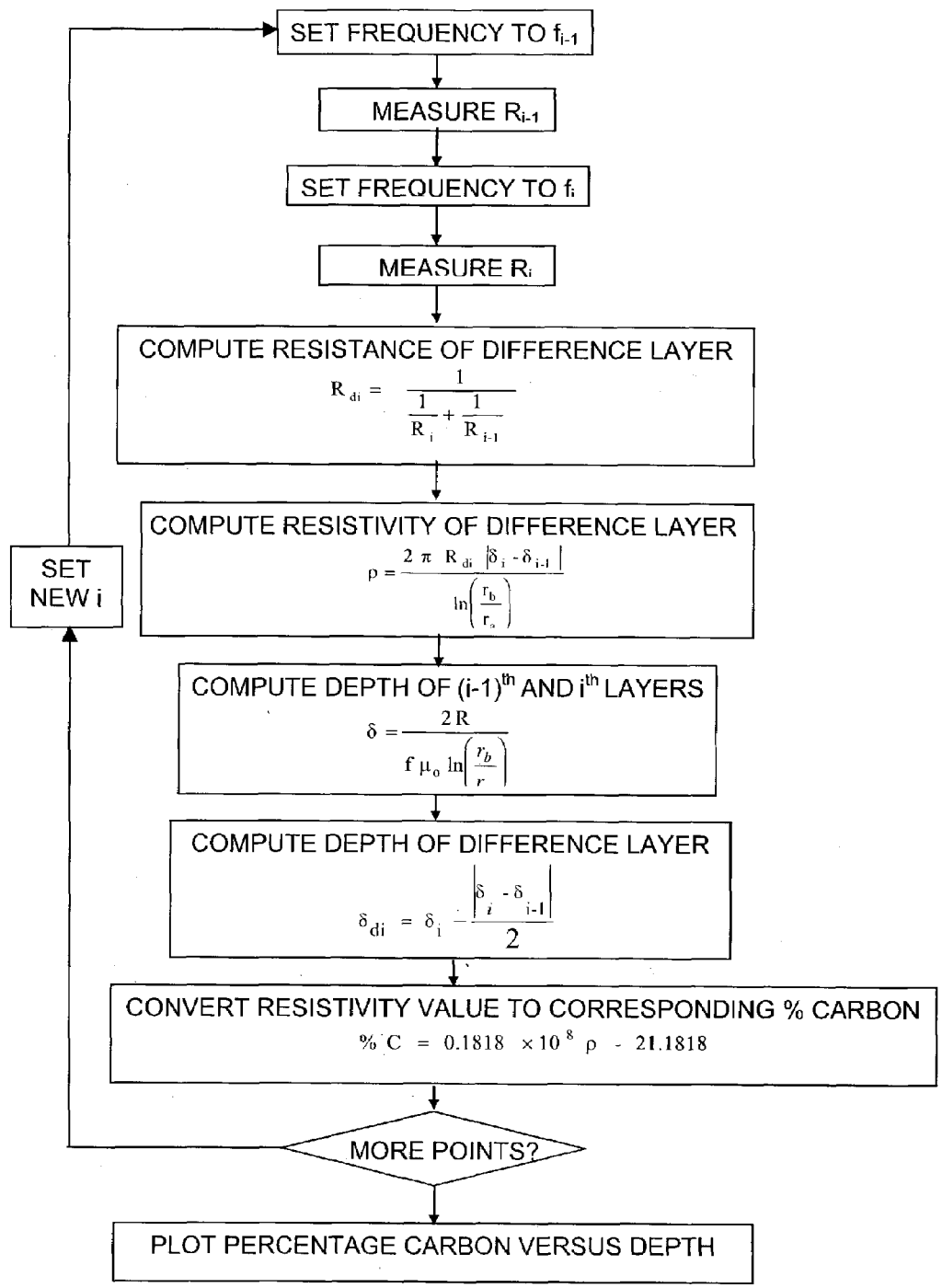
FIG. 9 is a flow chart for the concentric carbon profile measurement method of the present invention.
Figure 21:
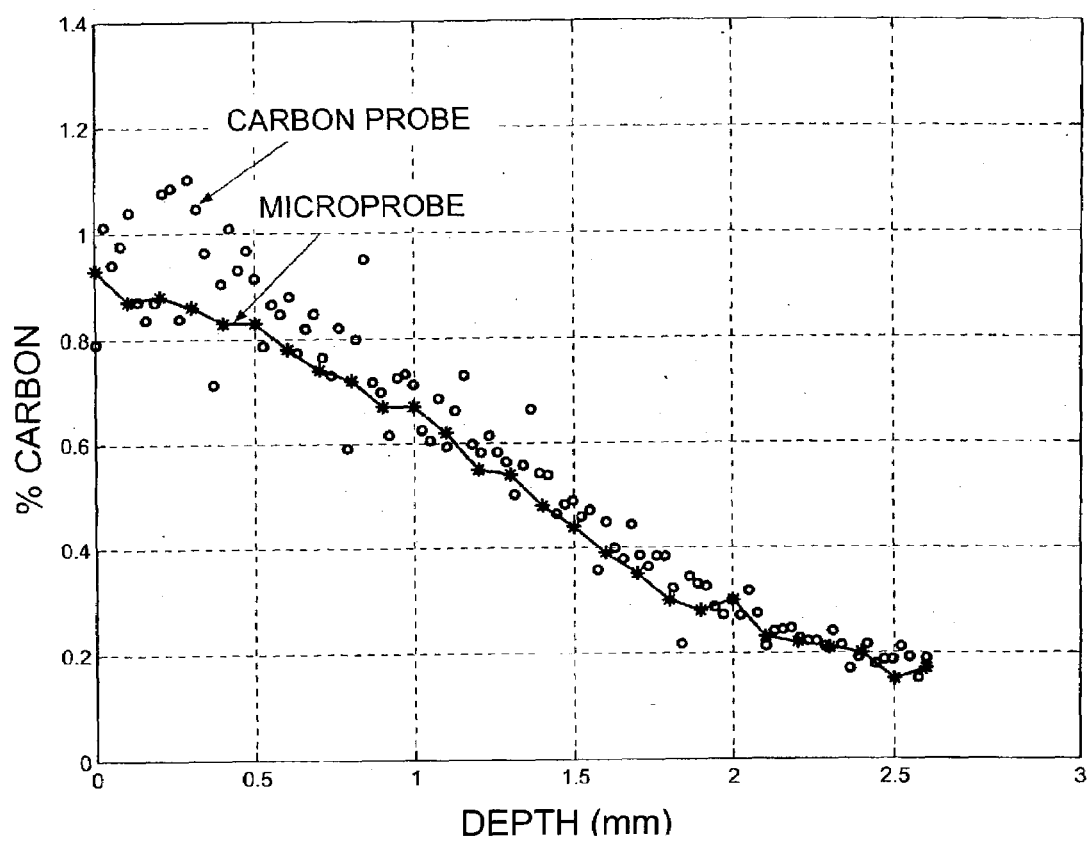
FIG. 21 is a plot of a carbon concentration profile of a carburized AISI 1018 steel sample measured at 870° C. with a concentric carbon sensor probe of the present invention.

As shown analytically above, the resistivity of the difference layer $R_{di}$ and its depth $\delta_{di}$ are computed by executing the sequence of setting the test frequency, measuring AC resistance, decrementing the test frequency, measuring the new AC resistance, computing the resistivity and depth of the difference layer, and converting the resistivity to a corresponding carbon content using an empirically-derived calibration equation, for example equation 1.29. The process is repeated to scan the alloy sample to the point of depth of interest and construct a carbon concentration profile. In FIG. 9 a flow chart summarizing the method and the algorithm used to construct a carbon concentration profile with a concentric electrode probe is provided. FIG. 21 compares a real-time, non-destructive carbon profile obtained with concentric sensor probe measurements with a carbon profile analytically measured on a cross-section of the same sample using electron microprobe analysis.

B. Rod-Shaped Probe

Details of sensor probe geometry, resistivity measurements, experimental configurations and measurement procedures are provided below for illustrating the resistivity measurement capabilities and solute concentration profiling capabilities of the rod-shaped sensor probe of the present invention.

1. Rod-Shaped Probe Design Considerations

Like the concentric electrode sensor probe discussed above, the rod-shaped sensor probe uses the AC skin effect for real-time, non-destructive measurement of alloy solute profiles in conductive materials, for example measurement of carbon concentration profiles in steel alloys during carburization processing. The rod-shaped sensor device comprises an alloy rod, fitted with a pair of voltage and current electrodes attached to opposing ends of the rod for measurement of AC resistance, resistivity profiles and solute profiles in sequestered subsurface volume elements of a conductive material during surface processing of sample components having similar composition, for example carbon concentration profiles during heat treatment processing of case hardened steels.

Figure 10A:
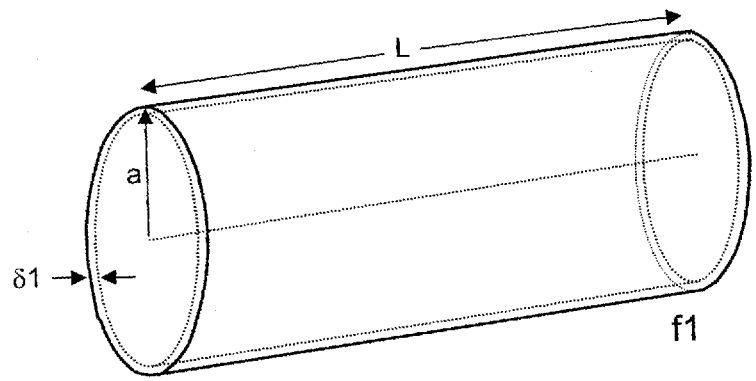
FIGS. 10A–10C show schematic representations of three distinct sample volumes sequestered at frequencies $f_1>f_2>f_3$ with a rod-shaped sensor probe where current penetration and sample volume depth increase with decreasing frequency.
Figure 10B:
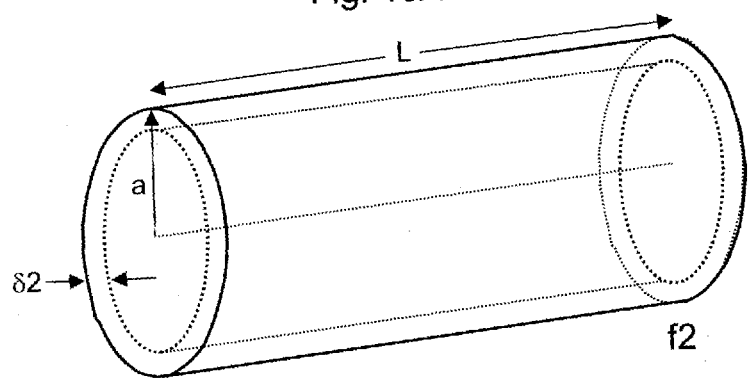
Figure 10C:
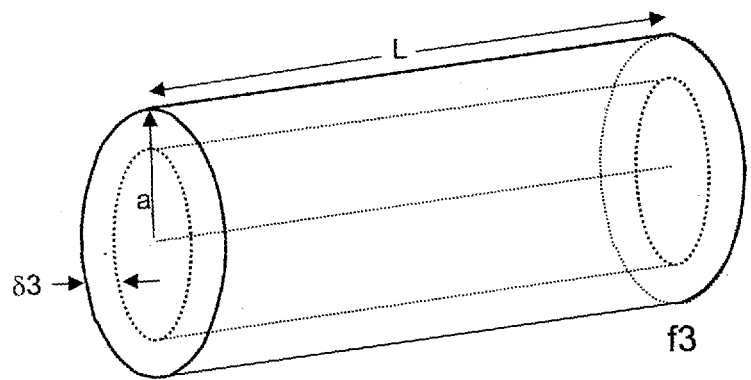

As with the concentric sensor probe discussed above, when AC current is applied at each end of a rod-shaped sensor probe, the depth of penetration of the applied current increases with increasing frequency due to the AC frequency-dependent "skin effect". By way of example, the sequestered sample volume in which the electric field and current are active is shown schematically in FIGS. 10A–10C at three different applied current frequencies where $f_1 > f_2 > f_3$ and the depth of current penetration increases with decreasing frequency. The electronically sequestered sample volumes are approximated as cylindrical shell-shaped regions which share the same external surface and outer diameter as the probe rod but whose depth or sample volume thickness varies with frequency such that greater current penetration and increased sample volume depth occurs at lower frequencies. It is important to note that FIG. 10A–10C is for illustration purposes only and the drawing is not to scale. The depth of penetration $\delta_i$ at each frequency is greatly exaggerated with respect to the radius a of the rod. As discussed above for the concentric sensor probe, the electric field has maximum strength at the surface of the conductive rod material. The magnitude of the electric field decays rapidly as the wave travels deeper into the rod. The depth of penetration z, normally expressed in skin depth units δ, is inversely proportional to the frequency such that the higher the frequency the lesser the wave penetration.

The sample volume element, which is defined by the rod geometry, electrode configuration and AC frequency, is established for each applied frequency and enables the generation of in-depth resistivity and solute concentration profiles from measurements made over a range of appropriate frequencies. It is important to note that there is electrical resistance, as seen by the applied source, only in the region where the field and current have finite magnitudes where the flow of electronic charge is being impeded by the rod electrical resistance. Thus, the sample volume which is responsible for the measured resistance is the volume element sequestered by the field created by the applied AC current at a given frequency. For the purpose of analytical and geometric simplification, this volume element is approximated as an cylindrical shell-shaped volume with an outer radius a and a depth or thickness z which is established at each applied current frequency and approximated by the skin depth δ at the applied frequency according to equations 1.32a or 1.32b below. As noted above, Rizzi and Rao have shown that this geometric approximation introduces negligible loss of accuracy in computation of the resistance of the sequestered sample volume element.

For determining the appropriate mathematical formulation for measuring resistance of a cylindrical alloy sample, consider a cylindrical rod of radius a and length L. When an AC voltage of a specified frequency is applied across the ends of the rod, the current flow is confined to an external surface layer having a frequency-dependent skin depth δ as discussed above. As noted above, Rizzi and Rao have demonstrated that the skin effect resistance may be computed by assuming that the total current is uniformly distributed over a thickness of a single skin depth δ [see P. Rizzi, *Microwave Engineering*, Prentice-Hall, Inc., Englewood Cliffs, N.J., 1988; N. Rao, *Basic Electromagnetics with Applications*. Prentice-Hall, Inc. Englewood Cliffs, N.J., 1972; H. Skilling, *Electric Transmission Lines*, McGraw-Hill Book Co. New York, 1951].

With AC measurements, the skin resistance is normally computed using the fundamental equation of resistance $$R = \rho \cdot \frac{L}{S} \quad (1.30)$$

where R is the resistance in Ohms, ρ is the electrical resistivity (in Ohms.meter) of the outer shell in which current is flowing, L is the length of the rod in meters, and S is the cross-sectional area of the shell in meters squared. The relation provided in equation 1.30 assumes that the rod radius dimension a is insignificant compared to the length L of the rod. If the ratio of the radius to length is significant, equation 1.30 can be modified by accounting for the contribution to the total resistance made by the two flat ends of the rod then $$R = \rho \frac{L}{S} + 2\rho \frac{\ln\left(\frac{a}{r}\right)}{2\pi\delta} \quad (1.31)$$

where a is the radius of the rod and r is the radius of the electrode, for example a conducting member such as a wire connector. The cross-sectional area S through which current flows within the skin depth δ may be computed by a simple surface integration to obtain $$S = 2\pi a\delta - \pi\delta^2$$

One can combine equation 1.31 above with equation 1.15 above for skin depth to obtain a more convenient expression for the skin depth:

$$\delta = \frac{2aR}{\mu f L + R} \quad (1.32a)$$

If the side resistance is taken into account then equation (1.32a) may be rewritten as $$\delta = \frac{2aR}{\mu f \left[L + 2a\ln\left(\frac{a}{r}\right)\right]} \quad (1.32b)$$

This expression permits the determination of the skin depth using measured AC resistance, signal frequency, and the rod's dimensions. Furthermore, the relative magnetic permeability of the steel reduces to unity in the carburizing temperature range above the Curie Temperature and the permittivity $\mu=\mu_0$ the permittivity of free space.

The resistivity is then obtained from equation (1.30) as $$\rho = \frac{RS}{L} \quad (1.34a)$$

where S is the effective cross-sectional area of the skin depth region of depth δ through which current passes along the length L of the rod.

If the side resistance is taken into account, then the expression for resistivity may be obtained by combining the value of the skin depth δ with equation 1.15 to obtain $$\rho = \frac{\pi\delta R}{\frac{L}{2a} + \ln\left(\frac{a}{r}\right)} \quad (1.34b)$$

Figure 11A:
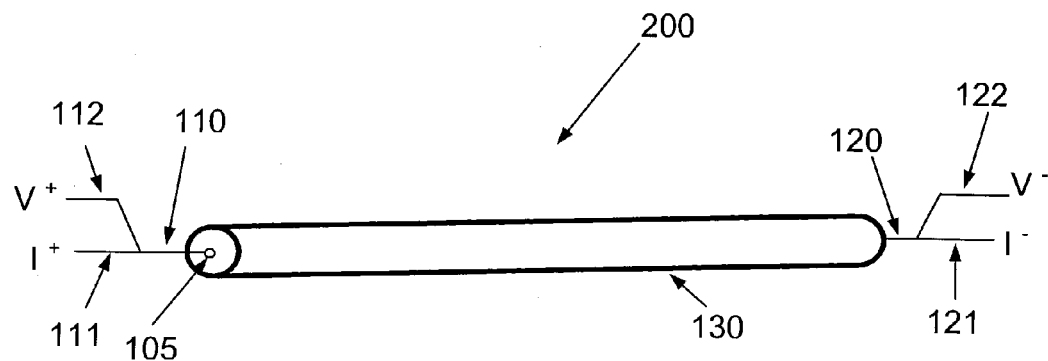
FIGS. 11A–11B show a schematic of one embodiment of a four wire rod-type probe connection (FIG. 11A) and an improved four wire connection embodiment (FIG. 11B) respectively.
Figure 11B:
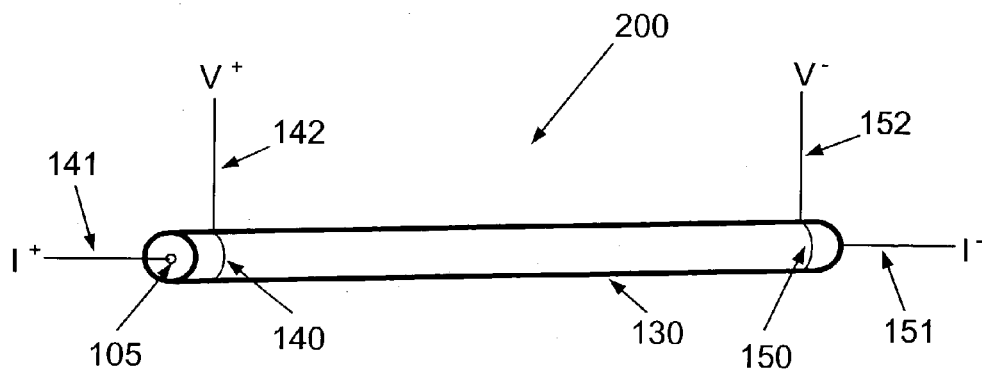

It is worth noting that if the electrode wire lead configuration shown in FIG. 11B is employed, the resistance of the rod ends can be ignored and equation 1.30 may be employed.

In preferred embodiments, the minimum radius a of the alloy rod 30 should be greater than the depth of penetration of the alloy solute being measured and the maximum radius a should be much less than the length L to ignore end resistance contributions to the total resistance. In the rod-shaped probe examples provided herein, an AWG #8 gauge electrode, or conductive member, with a radius of approximately 1.865 mm, an alloy rod radius of 1.27 cm and alloy rod length of 30.48 cm were employed. It is important to note, however, that the rod-shaped electrode probe of the present invention is not limited to these electrode lead and rod dimensions. The electrode, or conductive member, may be formed from a variety of cross-sectional shapes and conductive materials. While the actual size of the conductive member, rod radius and diameter may be adapted to virtually any component size, in preferred embodiments, the electrode, or conductive member, radius r is typically small relative to the rod radius a and the rod length L is typically large relative to the rod radius a.

FIG. 11A and FIG. 11B show two alternative rod-shaped sensor probe 200 embodiments employed for measuring AC resistance of carburized steel samples in the Austenite phase at 870° C. over a range of frequencies. For the rod-shaped sensor probes 200, a similar experimental configuration to that shown in FIG. 7 for the concentric probe sensor was employed where the assembly of the concentric electrodes (10,20), ceramic plate (70), insulators (75), clamps (80) and steel sample plate (60) were replaced by the simplified configuration of the rod-shaped probe 200. Methods employed for measuring the resistivity profile at various depths away from the alloy sample surface and constructing a carbon depth profile from the resistivity profile are discussed below. A flowchart of the measurement method employed with the rod-shaped probe is shown schematically in FIG. 12.

In one preferred embodiment shown in FIG. 11A, the rod-shaped probe assembly 200 comprises two sensor probe electrodes, a positive electrode 110 and negative electrode 120, which are fabricated from AWG#8 copper wire and inserted into holes 105 drilled in the opposing ends of an alloy rod 130. Due to the large thermal expansion coefficient of copper, upon heating the probe assembly 200 the expansion of the copper in the alloy rod hole 105 insures good electrical contact of the electrodes 110, 120 with the alloy rod 130 and minimizes electrical contact resistance. In this embodiment, the positive electrode 110 comprises a positive current lead 111 connected to the current output of an AC precision ohmmeter 50 and a positive voltage lead 112 connected to the positive voltage terminal of the ohmmeter 50. In this embodiment, the negative electrode 120 comprises a negative current lead 121 connected to the negative current terminal of an AC precision ohmmeter 50 and a negative voltage lead 122 connected to the negative voltage terminal of the ohmmeter 50. The electrode configuration for this embodiment is shown in FIG. 11A.

In an alternative preferred embodiment shown in FIG. 11B, the probe assembly 200 comprises four sensor probe electrodes, or conductive members, fabricated from AWG#8 copper wire, including a positive current electrode 141, a positive voltage electrode 140 and lead 142, a negative current electrode 151, and a negative voltage electrode 150 and lead 152. As with the embodiment shown in FIG. 11A, the positive and negative current electrodes 141, 151 are inserted into holes 105 drilled in the opposing ends of an alloy rod 130, ensuring good electrical contact upon heating due to the large thermal expansion coefficient of copper. In the embodiment shown in FIG. 11B, the positive and negative voltage electrodes 140, 150 are formed by wrapping an AWG#8 copper wire around the alloy rod 130 diameter to form ring-shaped, circular, conductive members or electrodes 140, 150 around the circumference of the rod 130 at opposing ends adjacent to the current electrodes 141, 151. For each ring-shaped voltage electrode 140, 150 a sufficient wire length is utilized to form positive and negative voltage leads 142, 152. In this embodiment, the positive current electrode 141 is connected directly to the current output of an AC precision ohmmeter 50 and the positive voltage lead 142 is connected to the positive voltage terminal of the ohmmeter 50. Similarly, the negative current electrode 151 is connected directly to the negative current terminal of an AC precision ohmmeter 50 and the negative voltage lead 152 is connected to the negative voltage terminal of the ohmmeter 50.

In preferred embodiments, where four electrodes are employed with the rod-shaped probe, the positive and negative voltage electrodes 142, 152 are tightly fitted around the circumference of the alloy rod 130 and the internal diameter of the electrodes 142, 152 match the outer diameter of the rod 130. In one sensor probe embodiment, where measurements of carbon profiles in carbon steel were made, a 30.48 cm long by 2.54 cm diameter rod of AISI 1095 carbon steel was employed as the alloy rod 130. Other alternative alloy rod diameters and lengths may also be employed.

In preferred embodiments, it is most desirable to choose an alloy rod composition which matches that of the component parts which are being processed to ensure accurate monitoring of resistivity and composition profiles in alloy components by eliminating any matrix effects which influence resistivity measurements. A wide variety of alloys materials may be employed as alloy rods 130. For example ferrous alloys, non-ferrous alloys, transition metal alloys, noble metal alloys, rare earth metal alloys, alkaline earth metal alloys and alloys of other metals such as aluminum, gallium, germanium, silicon, indium, tin, thallium, lead and bismuth may be employed as sensor probe rods 130 where it is desirable to measure concentration profiles of alloy solutes in these alloys and the solute elements of interest exhibit Matthiessen's Rule behavior.

2. Rod-shaped Probe Measurement Procedures

The AC resistance of the rod is measured and the carbon profile is determined using a similar method and algorithm as with the concentric electrode probes except for modification to the resistance and resistivity equations required because of the different probe geometry. Like the concentric electrode probe, the increase in carbon content of the alloy during heat treatment causes a proportional increase in the alloy resistivity. The rod sensor probe is exposed to the same carburizing atmosphere as processed components but is not in contact with any components. The resistivity is determined from measured AC resistance and the resistivity profile provides for the measurement of the alloy subsurface carbon profile. For greatest accuracy and optimum results, the rod sensor probe should be fabricated from the same alloy as the processed components that are being carburized and it should be placed in close proximity to the furnace components so as to ensure exposure of the rod to the same gas atmosphere as the components.

The processing algorithm used for the rod-shaped sensor probe is virtually identical to the algorithm presented for the concentric carbon probe except that the probe equations were modified for the different probe geometry and corresponding resultant resistance equations. The resistivity of the difference layer and its depth are computed by executing the sequence of setting the test frequency, measuring AC resistance, decrementing the test frequency, measuring the new AC resistance, computing the resistivity and depth of difference layer, and converting the measured resistivity to corresponding solute content by way of an empirically-derived solute calibration curve, for example the carbon conversion polynomial provided in equation 1.29. This process is repeated to scan the steel for a point of depth of interest and construct the solute profile versus depth for the sampled region.

Figure 12:
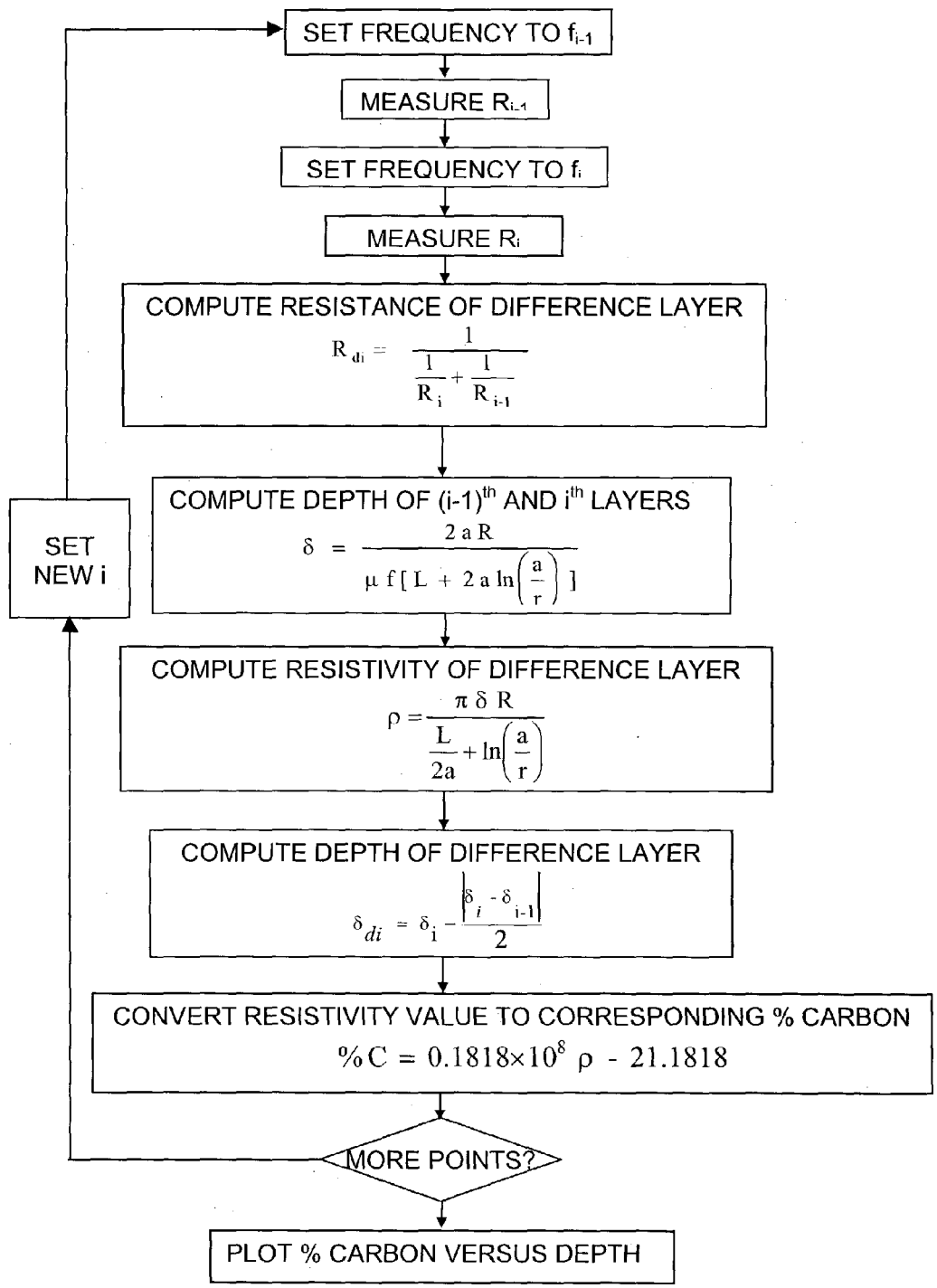
FIG. 12 is a flow chart for the rod-type carbon profile measurement method of the present invention.
Figure 22:
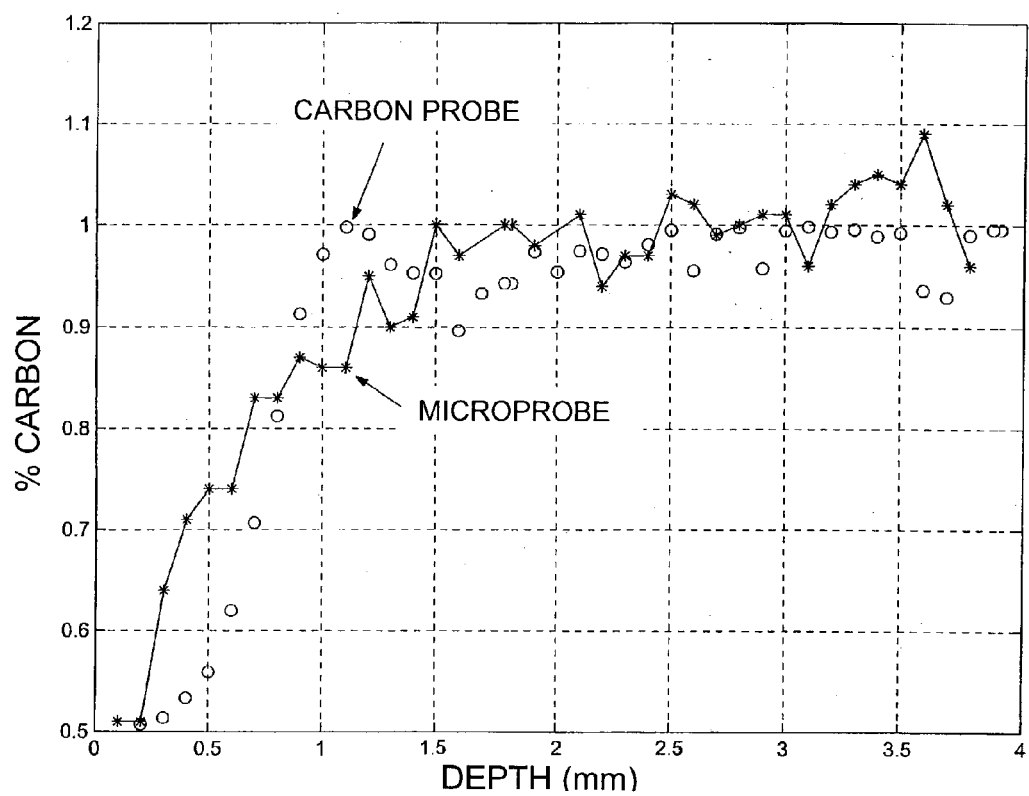
FIG. 22 is plot of a carbon concentration profile of a partially decarburized AISI 1095 steel sample measured at 870° C. with a rod-type carbon sensor probe of the present invention.

FIG. 12 is a flow chart showing the method and algorithm employed to construct a carbon depth profile for a steel rod sample. FIG. 22 is a plot comparing an alloy carbon profile measured with the real-time, non-destructive sensor probe and method of the present invention with a carbon profile measured after heat treating from a cut sample cross-section using electron microprobe analysis.

C. Resistivity Measurements

Sensor probe AC resistance and resistivity measurements were made employing the methods and procedures disclosed above using conventional precision LCR ohmmeters. While a typical ohmmeter uses a two-wire lead connection method for resistance measurement, this configuration is suitable only when lower precision measurements are acceptable and where the lead resistance is much smaller than the resistance of the element under test. For measurements made with the sensor probe and method of the present invention, where very high precision is required and very small resistances (i.e. much less than 1 Ohm) are to be measured, the common two-lead technique introduces a large error and is not suitable. The four-wire measurement technique eliminates the error inherent in the two-wire method and permits very precise measurements of elements whose resistances are very small. Both of these measurement techniques are described below.

1. Two Electrode/Four Wire Resistance Measurement Technique

Figure 13:
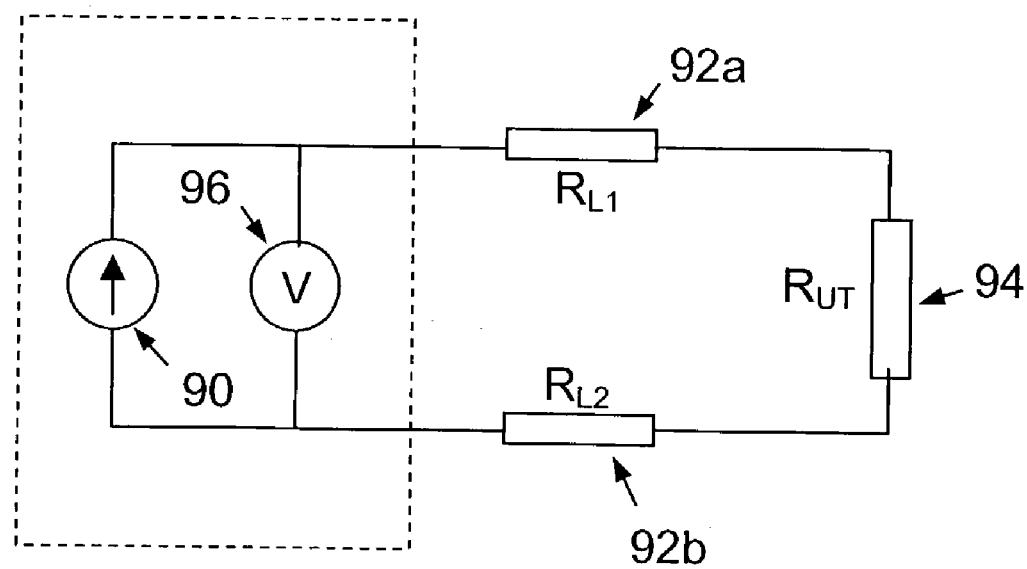
FIG. 13 is a schematic of an equivalent circuit for the two wire resistance measurement technique.

An equivalent circuit of a basic ohmmeter 50 which uses the two electrode, four wire technique is shown in FIG. 13. The ohmmeter 50 current source 90 provides a fixed current flow $I_C$ in the outer loop, through the undesired lead resistances 92a, 92b ($R_{L1}$ and $R_{L2}$) and the unknown resistance under test 94 ($R_{UT}$). No current flows through the voltmeter 96 because of its high input impedance. The current flow in the three resistors in series 92a, 92b, 94 causes a total voltage drop $$\Delta V_{TOTAL} = \Delta V_{R1} + \Delta V_{R2} + \Delta V_{UT}.$$

Upon application of a known current, the total voltage is measured by the voltmeter 96 and the total resistance is internally computed using Ohm's Law where $$R_{TOTAL} = \Delta V_{TOTAL}/I_c.$$

The resistance computed by the ohmmeter 50, $R_{TOTAL}$, is displayed on the ohmmeter 50 as the measured resistance where $$R_{measured} = R_{L1} + R_{L2} + R_{UT}.$$

If the test lead resistance $R_{L1}$ and $R_{L2}$ are not much smaller than the resistance of the element under test $R_{UT}$ then there may be a large error and diminished accuracy in the measured resistance $R_{measured}$.

FIG. 8A shows one embodiment of a two electrode, four wire concentric electrode probe assembly used in Example 2 below. FIG. 11A shows one embodiment of a two electrode, four wire rod-shaped probe assembly used in Example 1 and Example 3. Details of these two electrode probe assemblies are provided above. In these two electrode, four wire embodiments, the effects of the four lead resistance and contact resistance connections of the internal voltmeter 96 are eliminated. However, the effects of contact resistance of the current source 90 connection, although reduced by design, are not completely eliminated.

2. Four Electrode/Four Wire Resistance Measurement Technique

In a preferred embodiment, a four electrode, four wire concentric electrode probe (see FIG. 8B) is employed since this configuration eliminates the effect of contact resistance of the current source connection and thereby increases measurement accuracy. Similarly, FIG. 11B shows a preferred embodiment comprising a four electrode, four wire rod-shaped probe assembly for eliminating the effect of contact resistance of the current source connection and providing enhanced measurement accuracy. Details of these four electrode probe assemblies are provided above.

Figure 14:
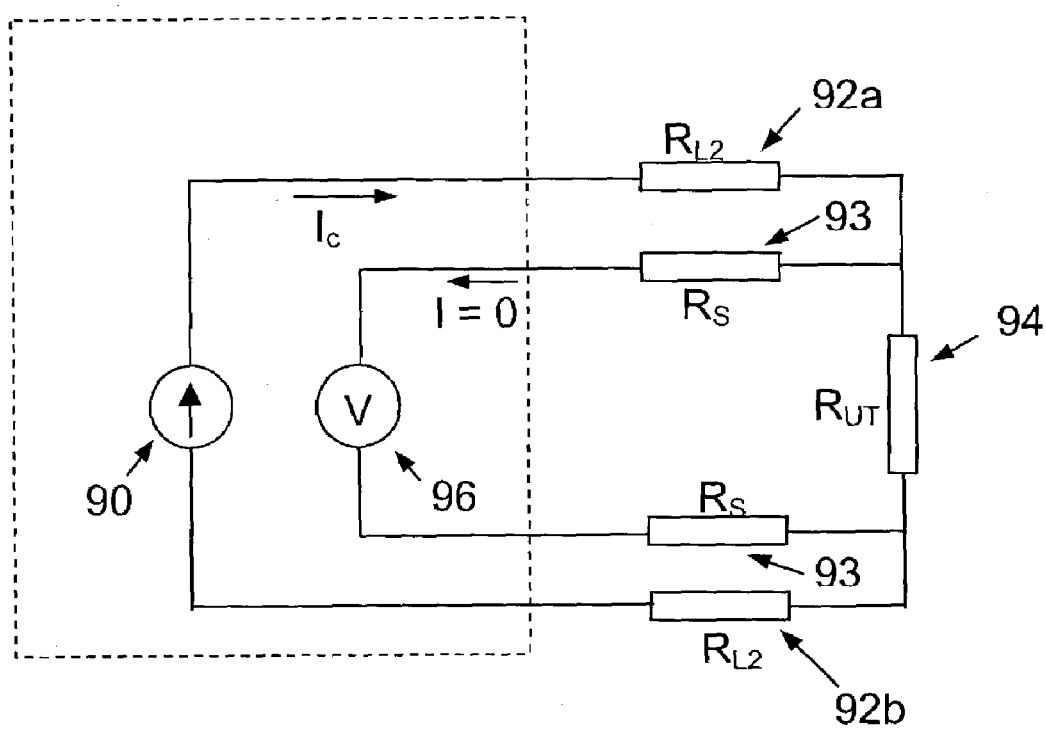
FIG. 14 is a schematic of an equivalent circuit for the four wire resistance measurement technique.

An equivalent circuit of an ohmmeter 50 which uses four electrode, four wire probes and measurement techniques is shown in FIG. 14. The outer pair of terminals provide the current source 90 connection, and the inner pair are the terminals across which the resistance under test $R_{UT}$ is presented. The resistance across the voltage measurement 96 terminals does not include the lead resistance of the current-carrying circuit 92a, 92b and is unaffected by the contact resistance at the current source 90 terminals and the minimal sensor resistance 93 ($R_S$). The current source 90 provides a fixed current flow $I_c$ through the lead resistances 92a, 92b ($R_{L1}$, and $R_{L2}$) and the unknown resistance under test 94 ($R_{UT}$). Negligible current flows through the voltmeter 96 because of its high input impedance (n.b. zero current for null methods) such that contact resistance of the voltage terminals is negligible (see M. B. Stout, *Basic Electrical Measurements*, 2$^{nd}$ Ed., Prentice Hall EE Series, Englewood Cliffs, N.J. 1960; E. Frank, *Electrical Measurement Analysis*. McGraw-Hill Book Company, New York, 1959). The voltage detected by the voltmeter 96 is the same as the voltage developed across the device under test 94 and the resistance computed by the ohmmeter 50 is obtained from Ohm's Law and displayed on the ohmmeter 50 as the measured resistance of the load under test $R_{UT}$.

With this four electrode, four wire probe and measurement configuration, the measured resistance is not affected by the lead resistance and contact resistance and the technique offers superior accuracy and is the preferred method for measuring small resistances. This technique has been successfully applied recently for detection of subsurface flaws in unsintered powder metallurgy compacts [see J. G. Stander et al., "Electrical Resistivity Testing of Green-State Powdered Metallurgy Compacts." *Review of Progress in Quantitative NDE*, Vol. 16B, p.2005–2012, Plenum Press, 1997; J. G. Stander et al., "A Novel Multi-Probe Resistivity Approach to Inspect Green-State Powder Compacts." *Journal of Nondestructive Evaluation*, Vol. 16, No. 4, p.205–214, 1997].

For the resistance measurements provided in Examples 1–3, an Agilent Technologies 4294A Precision Impedance Analyzer and Agilent 4285A and 4284A Precision LCR meters were employed. These meters exhibit high resolution and sensitivity and provide a host of additional features to assist in making more accurate resistance measurements including short and open circuit correction, averaging, and normal mode noise reduction. Since resistance measurement is generally considered highly reliable and repeatable only at the front panel of the micro-ohmmeter, considerable care has to be exercised in the fixturing, test lead fabrication and connection, and short and open compensation in order to enhance both the reliability and repeatability of actual sample measurements. The responsivity of the carbon sensor probe is excellent with a response time for resistance measurements and data processing of the order of minutes.

D. Carburizing System

This section describes a carburizing system configuration, algorithm and method which employ the carbon sensor probes of the present invention for automated control of a gas carburizing furnace and process.

A fully-automated system for the gas carburization of steel must combine several key elements including analytical and heuristic models of the carburization process, advanced sensors for direct process feedback, furnace automation and computer integration to real time intelligent controllers, and the creation and maintenance of a database of manufacturing process information. Using the sensor probe and method of the present invention, a gas carburizing system may be fully computer-controlled to produce a specific carbon profile within a target work part or component. The system uses direct process feedback from a sensor attached to a processed component. The control algorithm utilizes real time measurement of the actual case depth and a model-based determination of the first transition point between the boost stage and diffuse stage. The intelligent control system architecture, the computer integration and programming, and the furnace instrumentation are discussed below. A system which provides intelligent process control will diminish problems caused by the absence of direct feedback of the actual carbon profile.

Carburization is a process in which carbon is dissolved into the surface layer of steel. Carburizing, and subsequent quenching and tempering, produce a steel part with a strong, wear resistant surface [see *Carburizing and Carbonitriding*, American Society for Metals (Metals Park, Ohio) 1977]. Typically, during carburization a steel component is put into contact with an atmosphere of suitable carbon potential at elevated temperature. Initially, carbon is absorbed at the surface using a high carbon potential during a boost stage, then carbon diffuses into the steel using a lower carbon potential in a diffuse stage. Consequently, a distinct, finite carbon concentration profile is produced in the outer layer of the steel part. In actual practice, accurate matching of the produced carbon concentration profile to a desirable target carbon concentration profile is difficult to achieve. Significant impediments to process control include the inability to measure directly the actual carbon concentration profile in real-time and the inability to accurately determine the appropriate transition point between process boost and diffuse stages. By utilizing an intelligent carburization heat treatment control system which employs the real-time carbon sensor probe and method of the present invention, matching the actual component composition profile to the desired target profile may be readily achieved.

Figure 15:
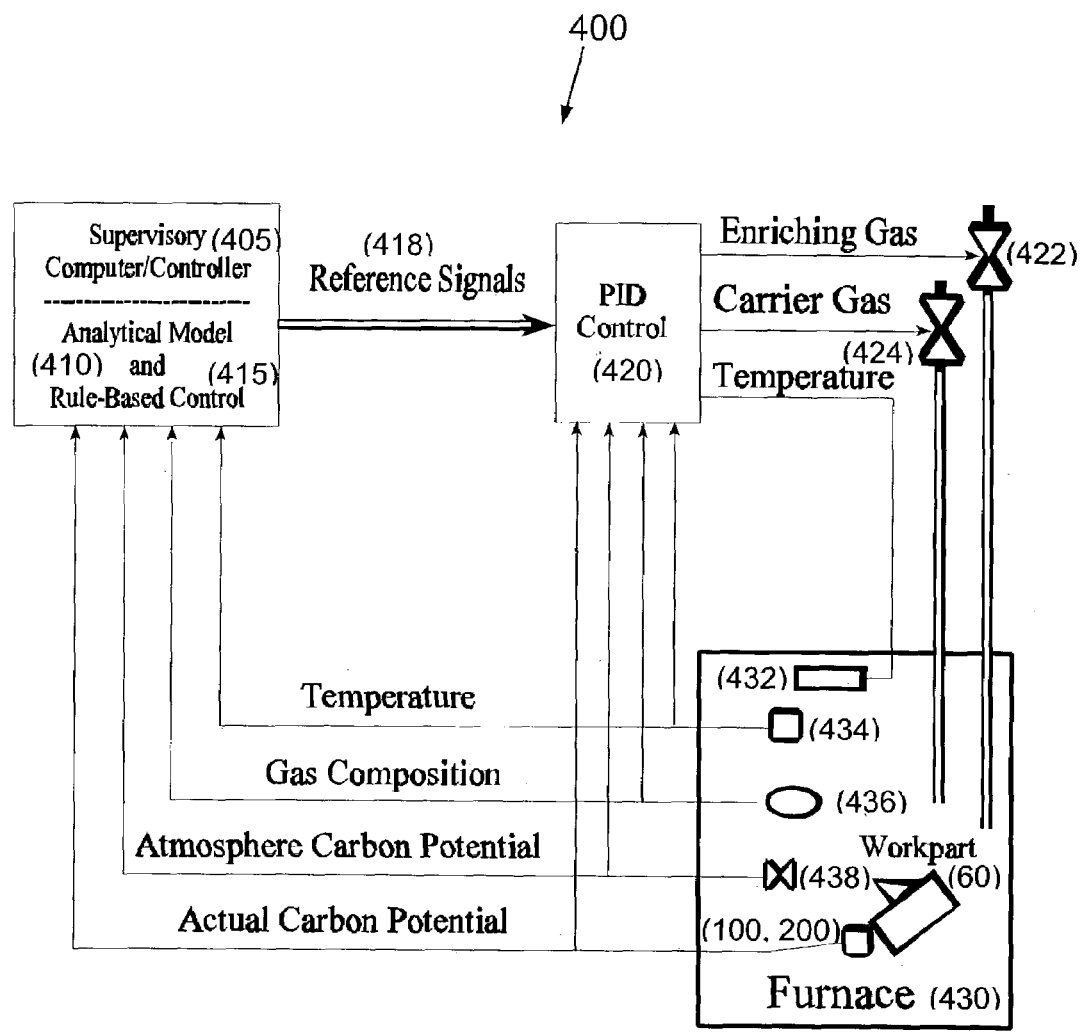
FIG. 15 is a schematic diagram of a heat treatment control system employing the carbon probe of the present invention.

The carbon sensor probe process control strategy is based on an analytical process model and a rule-based algorithm which utilizes the novel carbon sensor probe of the present invention for real-time measurement of carbon profiles. In one embodiment of an intelligent carburization heat treatment control system 400 shown schematically in FIG. 15, the system variables being measured and controlled are furnace temperature, furnace atmosphere carbon levels, actual carbon profile of the component workpiece, gas composition, and time.

An essential component of this system 400 is the carbon sensor probe 100, 200 and method disclosed herein which enables the direct, non-destructive, real-time measurement of carbon concentrations and surface profiles in steel alloys. In a preferred embodiment, the carbon sensor probes 100, 200 of the present invention are employed with an analytical process model 410 for carburization, for example a finite difference model developed to simulate the carburization process [see M. M. Makhlouf et al., *TMS-AIME Symposium on Intelligent Processing of Materials*, TMS-AIME (New Orleans, La.) 1991]. For a specified carbon profile, such a model 410 can be used iteratively to predict the theoretical required duration of the boost and diffuse stages. The model is initially provided with assumed input parameters, such as fixed temperatures, gas composition, mass transfer coefficient and a fixed or composition-dependent diffusion coefficient for each stage of the process. The input values of the process parameters utilized in simulation and the initial two-stage schedule predicted by the model 410 provide a supervisory controller 405 with the initial information to produce the appropriate initial reference signals to input into the PID controller 420 and initialize a rule-based control algorithm 415 which monitors furnace temperature, gas composition and carbon potential and component carbon levels for real-time adjustment of process conditions by way of the supervisory controller 405 and PID controller 420.

Figure 16:
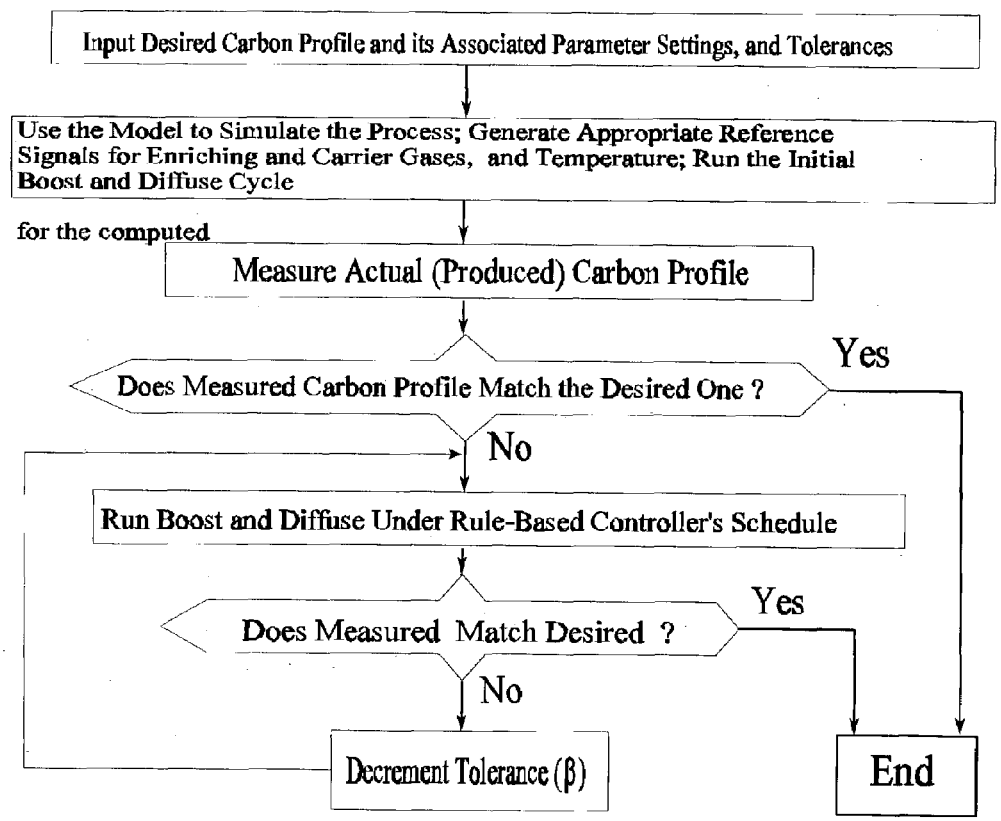
FIG. 16 shows a process control flow chart for the heat treatment control algorithm employed in the heat treatment control system of FIG. 15.

The schematic flowchart shown in FIG. 16 provides one embodiment of a control algorithm 415 employed with such a system 400. The supervisory controller 405 is provided input such as the desired carbon profile and the initial process parameters, such as temperatures, gas composition, mass transfer coefficient, and fixed or composition-dependent diffusion coefficient. Specific tolerances for these input variables may also be input. The supervisory controller 405 simulates the initial boost-diffuse cycle and provides reference signal outputs 418 to the PID controller 420 which are proportional to the target enriching gas mixture, carrier gas and temperature. The outputs 418 are initially provided for the duration of the boost stage and then for the duration of the diffuse stage. Due to the limitations of the model 410, process disturbances or decarburization losses which may occur in the process, the resulting actual carbon profile in the component workpiece may not match the targeted profile but will approximate the desired profile. A variety of process sensors are provided within the heat treating furnace 430, including a furnace control thermocouple 432, a furnace temperature thermocouple 434, a gas composition sensor 436, a gas phase carbon potential sensor 438, for example an oxygen gas sensor probe, and a carbon profile sensor 100, 200 of the present invention. These sensors provide feedback to both the Supervisory Controller 405 and PID controller 420 for process control. The PID controller 420 enables feedback control of processing conditions through the supervisory controller 405, a furnace control thermocouple 432 and process gas composition flow controllers, for example a carbon enriching gas controller 422 and carrier gas controller 422.

The resulting carbon profile in a component workpiece may be measured in real-time using the carbon sensor probe 100, 200 of the present invention and compared to the desired profile using a suitable analytical method and a rule-based control algorithm 415. For example, a graphical method such as those used by B. Edenhofer et al. may be utilized [see B. Edenhofer et al., "Heat Treatment and Surface Engineering-New Technology and Practical Applications," *Proceedings of the 6th International Congress on Heat Treatment of Materials*. World Materials Congress (Chicago. Ill.) 1988].

Figure 17:
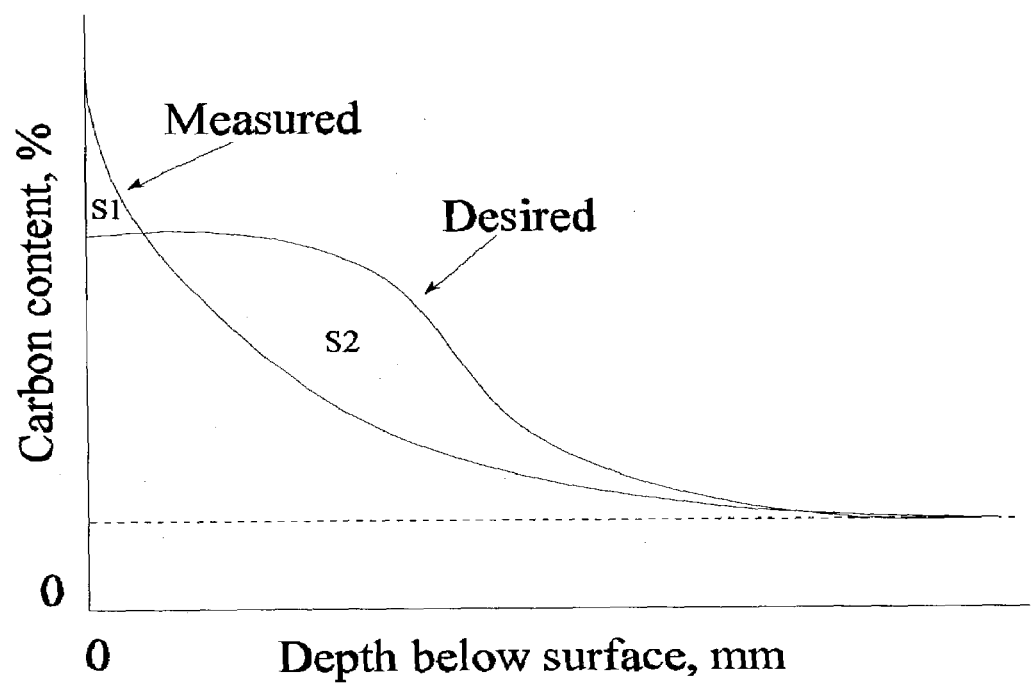
FIG. 17 shows a hypothetical measured and target carbon concentration profile for the heat treatment control system and algorithm.
Figure 18:
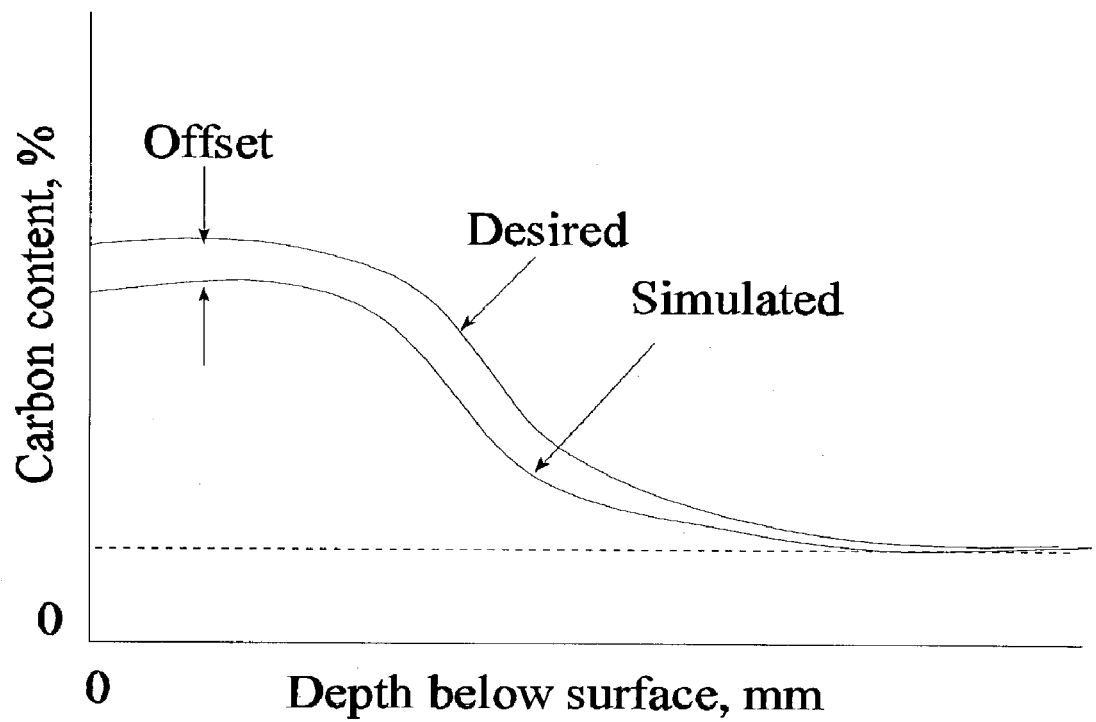
FIG. 18 shows a hypothetical simulated and target carbon concentration profile for the heat treatment control system and algorithm.
Figure 19A:
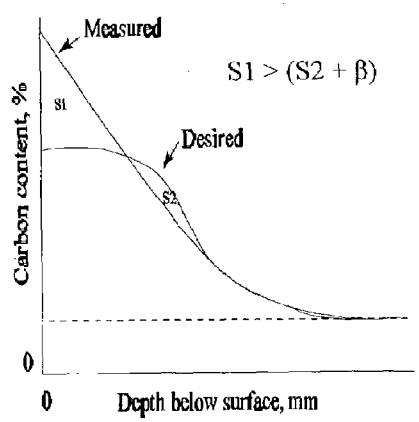
FIGS. 19A–19D shows hypothetical measured and target carbon concentration profiles for a rule-based algorithm employed with the heat treatment control system and algorithm to control carburization boost and diffuse cycles.
Figure 19B:
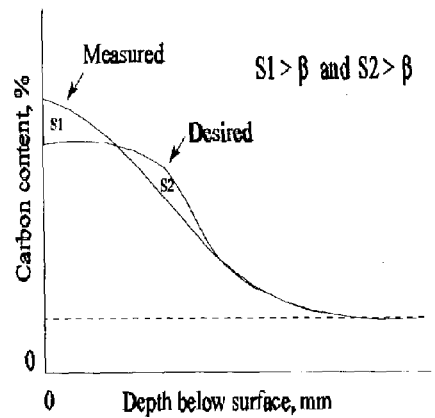
Figure 19C:
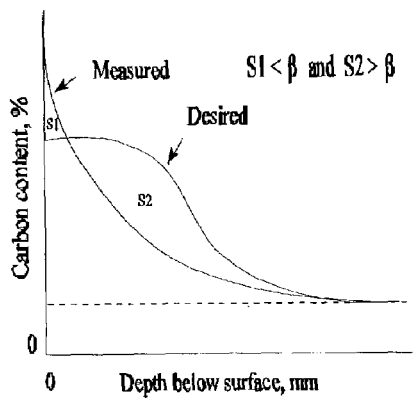
Figure 19D:
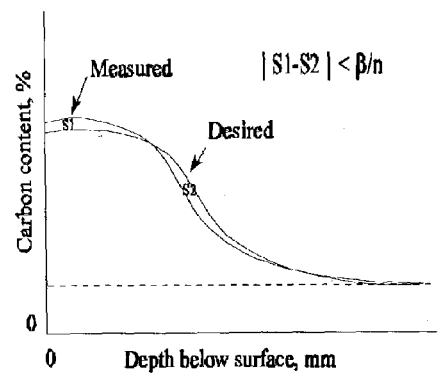

By way of example, with a graphical analytical method the areas under the desired and actual carbon profile curves are computed and subtracted from each other (see FIG. 17). The difference area S1 may be guaranteed to be smaller than the difference area S2 by having the supervisory computer simulate a pseudo-carbon profile curve which is identical to the desired curve except for the small negative offset (see FIG. 18). After the initial boost and diffuse cycle, the rule-based control algorithm takes over and the following control rules are applied:

1. If $S1>(S2+\beta)$, where $\beta$ is a specified tolerance expressed as an incremental surface area, then stop and signal over carburizing error (FIG. 19A);
2. While $S1>\beta$ and $S2>\beta$—resume or continue diffuse (FIG. 19B);

3. While S1<β and S2>β—resume or continue boost (FIG. 19C);
4. If S1−S2<β/n, then the process stops and the supervisory controller signals the end of carburization (FIG. 19D).

The rule-based algorithm 415 delineated above causes the system 400 to alternate back and forth between the boost and diffuse stages bringing the measured curve closer and closer to the desired curve. This insures that the actual or measured carbon profile matches the desired target profile. The smaller the tolerance β, the closer the match is to being an exact one.

The control system architecture 400, process model 410 and control algorithm 415 demonstrate how a gas carburizing furnace can be fully computer-controlled by employing the carbon sensor probe and method of the present invention to produce a specific carbon profile in its target workpiece. Since a computer can closely track the process in real-time, the process is freed from human intervention and traditional empirical methods of control. The system is self-adaptive in that, based on the real-time measurement of the actual carbon profile in the sample workpiece, the system can switch back and forth between the boost stage and diffuse stage until there is a precise match between the produced and desired carbon profiles. Because of this self-adaptive characteristic, the system can accommodate and correct for any process-related disturbances. The carburization data may be stored in a database for product certification, for statistical analysis, and for the development of an expert system. There are a number of additional benefits to this system such as the ability to provide full computerized documentation of all process variables and reduce labor costs. However, the principal impact of the system is to provide improved quality and reproducibility of carburized steel parts.

E. Additional Probe Applications

While emphasis has been placed on demonstrating applications of the sensor probe, system and methods of the present invention for measurement applications of carbon concentration profiles in steels, the device and method of the present invention are particularly suitable and may be readily employed in applications as a generic solute profile measurement probe for conductive alloys, as a process control sensor for induction heating treatments and as a sensor for detecting fatigue cracks in fatigue fracture measurements.

1. Alloy Solute Probes

While example applications of the sensor probe, method and system of the present invention have been provided for carbon sensors in monitoring carbon concentration profiles in carburized steel alloys and during carburizing heat treatments, other applications involving the deposition, sputtering, implantation, coating and diffusion of alloy solutes for surface treatment of alloys would advantageously benefit from the present invention where monitoring the concentration and diffusion profile of solute elements within alloy surface layers is required. For example, providing that an alloy solute displays Matthiessen's Rule behavior in a given alloy matrix, one skilled in the art may follow the teachings of the present invention to create sensor probes for measuring concentration profiles of a variety of alloy solutes, such as nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium, in various alloy materials, for example ferrous and non-ferrous alloys of iron, titanium, nickel, cobalt, manganese, molybdenum, tungsten, tantalum, niobium, zirconium, vanadium, aluminum, copper. tin, gold, silver, platinum and palladium.

2. Induction Heating Control

Induction heating involves placing an electrically conducting component workpiece in a time-varying electromagnetic field. The phenomenon is much like that of a transformer where a work coil represents the primary winding and the workpiece being heated represents the secondary winding. Electromagnetic energy is passed from the work coil to the workpiece by induction. As current flows through the work coil a strong field is established within the coil. The strength of the field depends on the magnitude of the current and on the coil design. In turn, the field induces an electric potential across the workpiece, and since the workpiece represents a closed circuit, the induced voltage forces a current, I, to flow in a closed-loop within the workpiece. The flow of current I and the resistance to the flow R cause heating by $I^2R$ losses. The induced current in the component is generally referred to as an "eddy current." The workpiece heats up because it has a resistance to the eddy current flow. The $I^2R$ heating of the workpiece is dependent on the magnitude of electric current flowing in the workpiece, the resistivity of the workpiece, and the depth of current penetration. Steel, which consists primarily of ferrite of bcc iron, is ferromagnetic up to its Curie temperature, and the rapid change in direction of the internal magnetization of domains in a steel within the field of the coil also generates considerable heat. When a ferritic steel transform to austenite, which is nonmagnetic, this contribution becomes negligible and the dominant factor becomes the $I^2R$ heating [see G. Krauss, *STEELS: Heat Treatment and Processing Principles*, $2^{nd}$ printing, ASM International, Materials Park, Ohio, 1990].

It should be noted that, as in a transformer, the frequency of the alternating current induced in the workpiece (secondary) has the same frequency as the alternating current in the work coil (primary). Thus the resistance R exhibited by the workpiece is an AC resistance which is the resistance of an outer layer of the workpiece according to the skin effect phenomenon. The thickness of the outer layer is dictated by the skin depth δ as explained above. Thus, high-frequency current is used when shallow heating and a thin case is desired, and intermediate or low frequencies are used when deep heating or a thick case is desired.

Typically, in induction heating, there is no uniform temperature distribution throughout the workpiece. This phenomenon is especially pronounced in the case of induction heating of alloys for surface hardening. During the heating stage, the surface layer of a carbon steel is hot enough to transform to austenite, the γ-Fe structure, while the subsurface region is still ferrite, α-Fe structure. When quenched, the austenitic surface layer transforms to a martensitic surface layer and becomes case hardened where the case depth is frequently defined as the surface region where the alloy microstructure is over 50% martensite. With appropriate quenching, the thickness of the austenitic surface layer dictates the thickness of the hardened case. Currently, there is no practical method for measuring the thickness of the austenitic surface layer during heating.

The duration of the heating stage of carbon steels is determined either empirically from experience or by off-line computer simulation [see G. Totten et al., (ed.); *Steel Heat Treatment Handbook*; Chapter 11, Rudnev et al., Marcel Dekker (New York 1997); *Induction Hardening and Tempering*, ASM Committee on Induction Hardening American Society for Metals (Metals Park, Ohio) 1964]. With the empirical method or simulation, it is difficult to apply real-time corrections for changes in the thermal and electromagnetic properties of the workpiece such as specific heat, thermal conductivity, relative magnetic permeability, and electrical resistivity during the heating cycle (see V. Rudnev et al., "Progress in Study of Induction Surface Hardening of Carbon." *Industrial Heating*; March 1996). Consequently, during heat treatments it is difficult to maintain a minimum case depth where shallow cases are required or to heat uniformly heat the workpiece where in-depth hardening is required.

During the heating stage, the electrical resistivity of steel alloys may change by a factor of 2 to 3. The greatest change occurs to the relative magnetic permeability $\mu_r$ which may change from a value of several thousands to a value of unity as the temperature of the surface layer reaches the Curie temperature of the workpiece. Thus, during the heating stage, the workpiece surface layer becomes nonmagnetic while its internal layer located just under the surface remains leading to bimetallic-type behavior. As the duration of the heating stage increases, heat progresses to the interior by conduction, the depth of heating increases, and the nonmagnetic (austenic) surface layer expands inward. Therefore the demarcation surface between the nonmagnetic layer and the magnetic layer is a dynamic one and shifts toward the core as the heating is maintained.

Due to variation in material properties, there is a step function change in the relative magnetic permeability and resistance resistivity just at the demarcation surface. A resistance profile measurement device, such as the sensor probe of the present invention, has the capability to scan the workpiece and measure the depth of the demarcation surface. Thus, the sensor probe of the present invention may be employed to measure the depth of an austenite surface layer in real-time so that heating may be stopped and quenching invoked at the appropriate time to produce a desired hardened case thickness. For such applications, the sensor probe may be appropriately miniaturized using conventional microelectronic methods and combined with a conventional control system which would provide for electronic switching of the power signal and sensor probe signal for heating and feedback control.

3. Fatigue Fracture Measurements

For fatigue fracture measurement applications, if a crack occurs anywhere within the alloy sample volume which is sequestered by the sensor probe of the present invention, it interferes with the flow of electrical current through the alloy volume and increases the measured resistance. The current practice of crack detection in alloys using DC resistance is typically limited to detecting the presence or absence of a crack. However, by providing for scanning the metal at various AC frequencies and hence varying the thickness of the sequestered, subsurface alloy sample volume, the device and method of the present invention may provide information on the depth as well as the size of a subsurface crack. Furthermore, if measurements are repeated at regular time intervals and they indicate that the resistance is increasing at a progressively higher rate, one may conclude that a fatigue fracture is propagating and be able to measure it in real-time during fatigue testing. Thus, the sensor probe and measurement method of the present invention would be particularly useful where nondestructive testing of a critical metal part is necessary to identify flaws that might lead to catastrophic failure during service.

EXAMPLE 1

Carbon Profile Calibration Measurements

Following the teachings of the present invention, the relationship between alloy electrical resistivity, in $\Omega.m$, and weight percent carbon was empirically determined from resistance measurements on an AISI 1095 carbon steel at 870° C.

As noted above, the experimental configuration used for generating a carbon calibration standard curve was a modified version of the configuration shown schematically in FIG. 7 where a two electrode, four wire rod-shaped sensor probe 200 (see FIG. 11A) and substitution technique were utilized to eliminate lead and contact resistances as potential sources of error. With this electrode configuration and measurement technique the ohmmeter's internal current source overcomes all series resistances and delivers a constant current through the two current leads. The internal high impedance voltmeter of the ohmmeter senses the voltage drop across the load and no contact or lead resistance is created by the voltage measurement because there is essentially no current flow in the voltage leads.

For calibration curve measurements the open-circuit and short-circuit compensation functions of the meter were executed to eliminate stray and residual impedances. An AISI 1095 steel rod was employed as a load in series with a calibrated resistive wire. The substitution technique was used for determining the alloy resistance with the calibrated resistive wire used as the boost or substitution resistor. This substitution technique is useful when measuring a low resistance that may approach or exceed the measurement limit of the meter. With this technique, a resistive wire having a large resistance was connected as the load, and its resistance $R_{substitution}$ was measured at a wide range of frequencies and recorded. The AISI 1095 alloy rod having a small resistance was then connected in series with the substitution resistor and the total resistance was measured at the same frequencies, $R_{total}=R_{steel}+R_{substitution}$. The net resistance of the alloy rod $R_{meas}$ was obtained by subtracting the first measurement $R_{substitution}$ from the second $R_{total}$.

For resistivity measurements, the AISI 1095 alloy rod was heated to 870° C. and the AC resistance was measured with a signal frequency of 500 Hz. At this low frequency, the skin depth is much larger than the rod radius of 12.7 mm and that the entire cross-section of the rod is penetrated by the current. Thus, the AC measurement conditions are similar to a DC current condition. The value of average resistivity was computed using equation 1.30. The resistivity was found to be $\rho=10^{-6}$ $\Omega.m$. Using this value of resistivity, the skin depths, $\delta_i$, at various frequencies, $f_i$, in the range of 20.9 kHz to 1.67 MHz were computed using equation 1.15.

The alloy rod was subsequently heated to 870° C. in an air atmosphere and was held at this temperature for 14 hours to allow considerable decarburization of the surface layer. The AC resistance of the rod was measured over a range of current frequencies from 20.9 kHz to 1.67 MHz. Typically, the ohmmeter was set at a fixed 10 mA or 20 mA current amplitude and measured the resultant voltage to calculate the resultant resistance. Resistance measurements were typically obtained from instrument averaging of 10 to 40 sample points. The resistivities at the different depths were computed using the algorithm for the rod-shaped sensor as discussed above. At the end of the 14-hour decarburizing cycle, the rod was rapidly quenched and the carbon concentration profile was measured using electron microprobe analysis technique. Measurement results are provided in Table 5 and represented graphically in FIG. 20 and analytically by the equation provided below.

TABLE 5

Measured resistance, computed resistivity and % C at depth.

| Frequency (Hz) | Resistance (Ohm) | Resistivity (Ohm-m) | Depth (m) | % C |
|---|---|---|---|---|
| 1.67e+6 | 5.41e−3 | 1.1941e−6 | 4.00e−4 | 0.51 |
| 1.05e+6 | 4.29e−3 | 1.1964e−6 | 5.00e−4 | 0.58 |
| 8.10e+5 | 3.77e−3 | 1.1987e−6 | 6.00e−4 | 0.60 |
| 5.79e+5 | 3.20e−3 | 1.2061e−6 | 7.00e−4 | 0.72 |
| 4.35e+5 | 2.78e−3 | 1.2119e−6 | 8.00e−4 | 0.88 |
| 3.66e+5 | 2.56e−3 | 1.2144e−6 | 9.00e−4 | 0.89 |
| 2.91e+5 | 2.29e−3 | 1.2177e−6 | 1.00e−3 | 0.94 |
| 2.53e+5 | 2.13e−3 | 1.2172e−6 | 1.10e−3 | 0.93 |
| 2.09e+5 | 1.95e−3 | 1.2160e−6 | 1.20e−3 | 0.96 |

Figure 20:
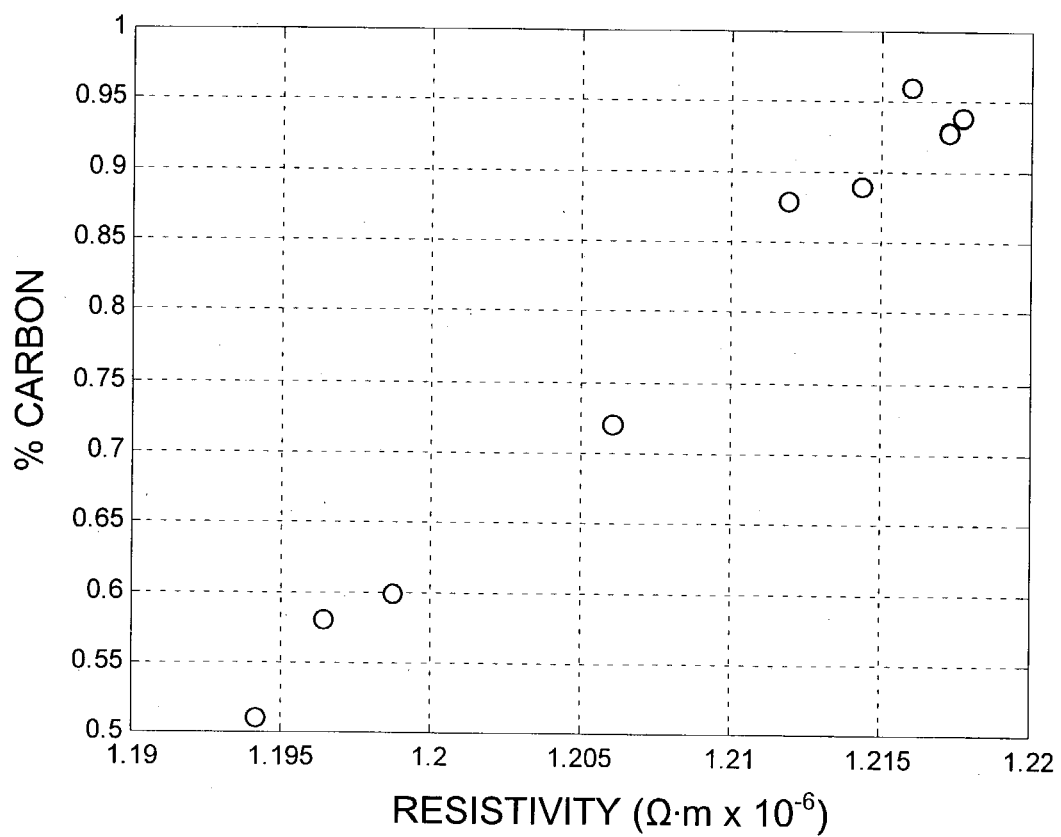
FIG. 20 is a plot of weight % carbon versus resistivity obtained from measurements at 870° C. on an AISI 1095 steel rod using a rod-type carbon sensor probe of the present invention.

As shown in FIG. 20, the empirical relationship between percentage carbon and resistivity was obtained by plotting % C at depth $\delta_i$ versus $\rho$ at the depth $\delta_i$ and finding the best fit equation for the data. This relationship was found to be % $C = 0.1818 \times 10^8 \rho - 21.1818$ which is consistent with Matthiessen's Rule.

EXAMPLE 2

Carbon Profiling with a Concentric Carbon Probe

Resistivity and carbon concentration profile measurements were performed on a 2.54 cm×20.3 cm ×.20.3 cm AISI 1018 steel alloy plate with a two electrode, four wire concentric sensor probe having an outer electrode diameter of 16 cm and an inner electrode diameter of 1 mm. The concentric probe assembly and inner 20 and outer 10 electrodes employed for these measurements are shown schematically in FIG. 4 and FIG. 8A. The experimental apparatus used for these measurements is shown schematically in FIG. 7. The concentric probe assembly, resistance measurement method and resistivity and carbon profiling methods are described above.

The AISI 1018 steel sample was a commercially available AISI1018 steel that had been previously carburized and quenched at Lindberg Heat Treating Corporation (Worcester, Mass.). An Agilent Technologies 4294A Precision Impedance Analyzer and the Agilent Technologies 4285A and 4284A Precision LCR meters were used for AC resistance measurements with a four wire Kelvin connection in four-terminal pair configuration. When switching from one meter to the other, only the BNC connection between the front-end panel of the Agilent instrument and the 4-lead Kelvin connectors set were switched; thus, measurement conditions, contact conditions and open/short compensation conditions were kept the same by maintaining all other connections untouched.

In order to reduce measurement errors and achieve correct measurement of resistance, it was necessary to provide open-circuit and short-circuit compensation to eliminate the effect of residual and stray impedances. A calibrated substitution resistive wire was also used in order to boost the reading well above the lower measurement range of the meters.

Prior to taking measurements all contact points and areas were cleaned to provide a smooth contact surface before use so as to minimize contact resistance. Proper calibration of the meter was achieved by executing appropriate short circuit, open circuit, and contact lead length compensation and corrections at temperature as generally known to those skilled in the art. Adequate mechanical pressure was maintained on the electrode-sample contact surfaces to ensure minimal contact resistance by means of the fixture and clamp configuration shown in FIG. 7.

A previously carburized AISI 1018 steel was reheated to 870° C., using a Thermolyne 30400 electric furnace, in order to anneal the sample in the austenite phase region,. This temperature is typical of a carburizing temperature and the annealing treatment ensured that the alloy would become paramagnetic with a relative magnetic permeability of unity regardless of the carbon gradient in the steel. During measurement, the furnace was turned off in order to eliminate internally generated interference and AC resistance measurements were rapidly taken and stored. The measurement data are plotted in FIG. 21.

In FIG. 21 real-time, non-destructive carbon concentration profiles measured with the concentric sensor probe of the present invention are compared with post-process, destructive analytical results obtained from electron microprobe analysis of sample cross-sections. The sensor probe measurements shown in FIG. 21 represent the average of 10 to 40 measurements. In FIG. 21, the best-fit curve and data points for the sensor probe measurements are shown as circles, while the electron microprobe measurements are shown as stars connected by straight lines. As shown in FIG. 21, the validity of the concentric carbon sensor probe and measurement method of the present invention is clearly demonstrated based on observed agreement between post-process, destructive electron microprobe analytical results and real-time, non-destructive sensor probe measurements.

EXAMPLE 3

Carbon Profiling with a Rod-Type Carbon Probe

Resistivity and carbon concentration profile measurements were performed on a 2.54 cm diameter by 30.48 cm long AISI 1095 steel alloy rod with a two electrode, four wire rod-shaped sensor probe. The probe assembly 200 employed for these measurements is shown schematically in FIG. 11A and the probe assembly, resistance measurement method and resistivity and carbon profiling methods are described above. As noted above, care was exercised to eliminate or diminish resistance measurement errors due to contact resistance, lead-length differences, and improper meter calibration. A calibrated substitution resistive wire was used as employed above.

For these measurements, a Thermolyne-30400 heat treating furnace was used to heat the probe assembly to 870° C. in an air atmosphere. The alloy rod was held at temperature for 16 hours to produce considerable decarburization of the surface layer by oxygen in the air atmosphere. During the heating of the furnace from room temperature to 870° C., the meter's oscillator was set to 1 MHz and AC resistance was measured continuously; it was observed that in the vicinity of 790° C. there was an exceptionally sharp rise in the resistance followed by a sharp drop, then a slow rise again. This behavior is attributed to the AISI 1095 steel undergoing a crystallographic or magnetic transformation at temperatures approaching the Curie temperature.

After the rod decarburized for 16 hours at 870° C. temperature, AC resistance measurements were taken and recorded over an AC current frequency span of 20 kHz to 4 MHz. To cover this frequency span, Agilent Technologies 4284A and 4285A Precision LCR meters were employed with a two electrode, four wire Kelvin connection comprising two current contacts and two potential contacts. For these measurements, instrument current amplitude was fixed at either 10 mA or 20 mA and voltage was measured to calculate sample resistance. Sample points were taken from an averaging of 10 to 40 points. The analytical processing algorithm employed in these measurement was virtually identical to the algorithm utilized for the concentric carbon probe except that the probe equations were modified due to probe geometry, resistance and resistivity calculations as discussed above.

The resistivity of the difference layer and its depth were computed by executing the sequence of set test frequency, measure AC resistance, decrement test frequency, measure new AC resistance, compute resistivity and depth of difference layer, and convert resistivity to corresponding carbon content. The process was repeated for each skin depth of interest and results were used to construct the carbon profile versus depth for the sample. FIG. 12 is a flow chart summarizing the method and the algorithm used to construct the carbon versus depth profile. FIG. 22 compares a carbon profile obtained with electron microprobe microanalysis with the measured carbon profile using the method rod probe sensor. As shown by the data in FIG. 22, the good agreement between post-process, destructive electron microprobe analytical results and real-time, non-destructive sensor probe measurements demonstrate the validity of the rod-type probe sensor, measurement method and measurement system of the present invention.

Having described the preferred embodiments of the invention, it will now become apparent to one of skill in the art that other embodiments incorporating the disclosed concepts may be used. Therefore, it is not intended to limit the invention to the disclosed embodiments but rather the invention should be limited only by the spirit and scope of the following claims.

What is claimed is:

1. A solute sensor probe for measuring a solute concentration profiles in a conductive material by sequestering and sampling a plurality of defined subsurface volume elements, said sensor probe comprising:
   at least one first electrode for contacting a first portion of an external surface of said material, said first electrode defining a first boundary surface of each of said sampled volume elements;
   at least one second opposing electrode for contacting a second portion of said external surface, said second electrode in coaxial alignment with said first electrode, said second electrode defining a second boundary surface of each of said sampled volume elements;
   said first and second electrodes being adapted for receiving an alternating current source, said current source configured for providing a plurality of alternating current frequencies to said electrodes;
   said first and second electrodes being adapted for measurement of a plurality of voltage potentials established between said electrodes by application of said alternating current at said plurality of said frequencies;
   a plurality of third boundary surfaces of each of said sampled volume elements, each one of said third boundary surfaces positioned at a unique, frequency-dependent depth $\delta_i$ below said external surface where $$\delta = \frac{1}{\sqrt{\mu\sigma\pi f}},$$

μ is the material magnetic permeability, σ is the material conductivity and $f_i$ is one of said alternating current frequencies, each one of said sampled volume elements being bounded by a region enclosed by said first and second boundary surfaces, one of said frequency-dependent third boundary surfaces and the external surface of said material; and
   a solute concentration correlation means for determining the solute concentration of each of said sampled volume elements from a measured resistivity of each sampled volume element, said resistivity of each volume element being derived from said applied current and said measured voltage at one of said plurality of frequencies.

2. The sensor probe of claim 1 wherein said first electrode comprises an outer circular conductor for contacting said first portion of said external surface and said second electrode comprises an inner circular conductor for contacting said second portion of said external surface, said outer conductor having an inner radius which is greater than an outer radius of said inner conductor, said outer conductor being concentrically aligned with said inner conductor.

3. The sensor probe of claim 2 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

4. The sensor probe of claim 2 where said solute is carbon and said conductive material is a ferrous alloy.

5. The sensor probe of claim 1 wherein said first electrode comprises a first conductive member in electrical contact with a proximal end of a rod formed from said conductive material and said second electrode comprises a second conductive member in electrical contact with a distal end of said rod, said first and second conductive members and said rod being co-axially aligned with one another.

6. The sensor probe of claim 5 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

7. The sensor probe of claim 5 where said solute is carbon and said conductive material is a ferrous alloy.

8. A solute sensor probe for sequestering and sampling a plurality of defined subsurface volume elements in a conductive material, said sensor probe comprising:
   a first voltage electrode for contacting a first portion of an external surface of said material, said first voltage electrode defining a first boundary surface of each of said sample volume elements;

a second opposing voltage electrode for contacting a second portion of said external surface, said second voltage electrode in coaxial alignment with said first voltage electrode, said second voltage electrode defining a second boundary surface of each of said sample volume elements;

a first current electrode for contacting a third portion of said external surface, said first current electrode positioned adjacent to said first voltage electrode and in coaxial alignment with said first and second voltage electrodes;

a second opposing current electrode for contacting a fourth portion of said external surface, said second current electrode positioned adjacent to said second voltage electrode and in coaxial alignment with said first current electrode and said first and second voltage electrodes;

said first and second current electrodes being adapted for receiving an alternating current source, said current source configured for providing a plurality of alternating current frequencies to said electrodes;

said first and second voltage electrodes being adapted for measurement of a plurality of voltage potentials established between said voltage electrodes by application of said alternating current to said current electrodes at said plurality of said frequencies;

a plurality of third boundary surfaces of each of said sampled volume elements, each one of said third boundary surfaces positioned at a unique, frequency-dependent depth $\delta_i$ below said external surface where $$\delta = \frac{1}{\sqrt{\mu\sigma\pi f}},$$

μ is the material magnetic permeability, σ is the material conductivity and $f_i$ is one of said alternating current frequencies, each one of said sampled volume elements being bounded by a region enclosed by said first and second boundary surfaces, one of said frequency-dependent third boundary surfaces and the external surface of said material; and a solute concentration correlation means for determining the solute concentration of each of said sampled volume elements from a measured resistivity of each sampled volume element, said resistivity of each volume element being derived from said applied current and said measured voltage at one of said plurality of frequencies.

9. The sensor probe of claim 8 wherein
said first current electrode comprises a first outer circular conductor having an inner radius;
said first voltage electrode comprises a second outer circular conductor having an inner and outer radius, said first outer conductor inner radius being greater than said second outer conductor outer radius;
said second voltage electrode comprises a first inner circular conductor having an inner and outer radius, said first inner conductor outer radius being less than said second outer conductor inner radius; and
said second current electrode comprises a second inner circular conductor having an outer radius, said first inner conductor inner radius being greater than said second inner conductor outer radius.

10. The sensor probe of claim 9 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

11. The sensor probe of claim 9 where said solute is carbon and said conductive material is a ferrous alloy.

12. The sensor probe of claim 8 wherein
said first current electrode comprises a first conductive member in electrical contact with a proximal end of a rod formed from said conductive material;
said first voltage electrode comprises a first ring-shaped conductive member in electrical contact with a first diameter of said rod, said first rod diameter adjacent to said first conductive member at said proximal rod end;
said second current electrode comprises a second conductive member in electrical contact with a distal end of said rod; and
said second voltage electrode comprises a second ring-shaped conductive member in electrical contact with a second diameter of said rod, said second rod diameter adjacent to said second conductive member of said distal rod end.

13. The sensor probe of claim 12 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

14. The sensor probe of claim 12 where said solute is carbon and said conductive material is a ferrous alloy.

15. A system for measuring solute concentration profiles in a conductive material during thermal processing, said system comprising:
a solute sensor probe for measuring solute concentration profiles in a conductive material by sequestering and sampling a plurality of defined subsurface volume elements, said sensor probe comprising:
at least one first electrode for contacting a first portion of an external surface of said material, said first electrode defining a first boundary surface of each of said sampled volume elements;
at least one second opposing electrode for contacting a second portion of said external surface, said second electrode in coaxial alignment with said first electrode, said second electrode defining a second boundary surface of each of said sampled volume elements;
said first and second electrodes being adapted for receiving an alternating current source, said current source configured for providing a plurality of alternating current frequencies to said electrodes;

said first and second electrodes being adapted for measurement of a plurality of voltage potentials established between said electrodes by application of said alternating current at said plurality of said frequencies;

a plurality of third boundary surfaces of each of said sampled volume elements, each one of said third boundary surfaces positioned at a unique, frequency-dependent depth $\delta_1$ below said external surface where $$\delta = \frac{1}{\sqrt{\mu\sigma\pi f}},$$

$\mu$ is the material magnetic permeability, $\sigma$ is the material conductivity and $f_i$ is one of said alternating current frequencies, each one of said sampled volume elements being bounded by a region enclosed by said first and second boundary surfaces, one of said frequency-dependent third boundary surfaces and the external surface of said material; and a solute concentration correlation means for determining the solute concentration of each of said sampled volume elements from a measured resistivity of each sampled volume element, said resistivity of each volume element being derived from said applied current and said measured voltage at one of said plurality of frequencies;

a heat treating furnace having a gas composition controller and temperature controller;

a supervisory controller for storing process parameters, receiving input signals from said gas composition and temperature controllers and said solute sensor probe, and generating reference signal outputs to said gas composition and temperature controllers;

a process model algorithm for providing said supervisory controller with initial process parameters to generate initial reference signal outputs for said temperature and gas composition control;

a rule-based control algorithm for controlling said supervisory controller by monitoring said sensor probe output, temperature and gas composition, and instructing said supervisory controller to modify said process parameters by adjusting reference signal output to said gas composition and temperature controllers; and a PID controller for receiving said supervisory controller reference signal output and controlling said furnace temperature and gas composition.

16. The system for measuring solute concentration profiles of claim 15 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

17. The system for measuring solute concentration profiles of claim 15 where said solute is carbon and said conductive material is a ferrous alloy.

18. The system for measuring solute concentration profiles of claim 15 wherein said solute sensor probe further comprises:

a first voltage electrode for contacting a first portion of an external surface of said material, said first voltage electrode defining a first boundary surface of each of said sample volume elements;

a second opposing voltage electrode for contacting a second portion of said external surface, said second voltage electrode in coaxial alignment with said first voltage electrode, said second voltage electrode defining a second boundary surface of each of said sample volume elements;

a first current electrode for contacting a third portion of said external surface, said first current electrode positioned adjacent to said first voltage electrode and in coaxial alignment with said first and second voltage electrodes; and a second opposing current electrode for contacting a fourth portion of said external surface, said second current electrode positioned adjacent to said second voltage electrode and in coaxial alignment with said first current electrode and said first and second voltage electrodes.

19. The system for measuring solute concentration profiles of claim 18 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

20. The system for measuring solute concentration profiles of claim 18 where said solute is carbon and said conductive material is a ferrous alloy.

21. A method for measuring solute concentration profiles in a conductive material by sequestering and sampling a plurality of defined subsurface volume elements comprising the steps of:

providing a solute sensor probe comprising:
at least one first electrode for contacting a first portion of an external surface of said material, said first electrode defining a first boundary surface of each of said sampled volume elements;

at least one second opposing electrode for contacting a second portion of said external surface, said second electrode in coaxial alignment with said first electrode, said second electrode defining a second boundary surface of each of said sampled volume elements;

said first and second electrodes being adapted for receiving an alternating current source, said current source configured for providing a plurality of alternating current frequencies to said electrodes;

said first and second electrodes being adapted for measurement of a plurality of voltage potentials established between said electrodes by application of said alternating current at said plurality of said frequencies;

a plurality of third boundary surfaces of each of said sampled volume elements, each one of said third boundary surfaces positioned at a unique, frequency-dependent depth δ, below said external surface where $$\delta = \frac{1}{\sqrt{\mu\sigma\pi f}},$$

μ is the material magnetic permeability, σ is the material conductivity and $f_i$ is one of said alternating current frequencies, each one of said sampled volume elements being bounded by a region enclosed by said first and second boundary surfaces, one of said frequency-dependent third boundary surfaces and the external surface of said material; and a solute concentration correlation means for determining the solute concentration of each of said sampled volume elements from a measured resistivity of each sampled volume element, said resistivity of each volume element being derived from said applied current and said measured voltage at one of said plurality of frequencies;

contacting said conductive material with said sensor probe;

applying a first alternating current at a first frequency to said probe electrodes;

measuring a first resistance at said first frequency;

applying a second alternating current at a second frequency to said probe electrodes;

measuring a second resistance at said second frequency;

computing a first difference layer resistance for said first and second resistances;

calculating a first difference layer resistivity for said difference layer;

computing a depth for said first and second resistance measurements and for said first difference layer;

calculating a first solute concentration from said computed first difference layer resistivity;

assigning said solute concentration to said first difference layer computed depth; and incrementing said first and second current frequencies and repeating said applying a first current, said measuring a first resistance, said applying a second current, said measuring a second resistance, said computing a first difference layer resistance, said calculating a first difference layer resistivity, said computing a depth, said calculating a solute concentration, and said assigning said solute concentration steps until the calculated resistivity at adjacent difference layers are equal.

22. The method of claim 21 wherein said first electrode comprises an outer circular conductor for contacting said first portion of said external surface and said second electrode comprises an inner circular conductor for contacting said second portion of said external surface, said outer conductor having an inner radius which is greater than an outer radius of said inner conductor, said outer conductor being concentrically aligned with said inner conductor; and said computing said difference later resistivity step further comprises calculating said resistivity from said difference layer resistance $R_{di}$ and thickness $|\delta_i-\delta_{i-1}|$, said outer conductor radius $r_b$ and said inner conductor radius $r_a$ where said resistivity is given as $$\rho = \frac{2\pi R_{di}|\delta_i - \delta_{i-1}|}{\ln\left(\frac{r_b}{r_a}\right)}.$$

23. The method of claim 21 wherein said first electrode comprises a first conductive member in electrical contact with a proximal end of a rod formed from said conductive material and said second electrode comprises a second conductive member in electrical contact with a distal end of said rod, said first and second conductive members and said rod being co-axially aligned with one another; and said computing said difference later resistivity step further comprises calculating said resistivity from said sample volume resistance R and depth δ, said rod radius a and said conductive member radius r where said resistivity is given as $$\rho = \frac{\pi\delta R}{\frac{L}{2a} + \ln\left(\frac{a}{r}\right)}.$$

24. The method of claim 21 wherein said providing step further comprises a solute sensor probe having a first voltage electrode for contacting a first portion of an external surface of said material, said first voltage electrode defining a first boundary surface of each of said sample volume elements;

a second opposing voltage electrode for contacting a second portion of said external surface, said second voltage electrode in coaxial alignment with said first voltage electrode, said second voltage electrode defining a second boundary surface of each of said sample volume elements;

a first current electrode for contacting a third portion of said external surface, said first current electrode positioned adjacent to said first voltage electrode and in coaxial alignment with said first and second voltage electrodes; and a second opposing current electrode for contacting a fourth portion of said external surface, said second current electrode positioned adjacent to said second voltage electrode and in coaxial alignment with said first current electrode and said first and second voltage electrodes.

25. The method of claim 24 wherein said first current electrode comprises a first outer circular conductor having an inner radius;

said first voltage electrode comprises a second outer circular conductor having an inner and outer radius, said first outer conductor inner radius being greater than said second outer conductor outer radius;

said second voltage electrode comprises a first inner circular conductor having an inner and outer radius, said first inner conductor outer radius being less than said second outer conductor inner radius;

said second current electrode comprises a second inner circular conductor having an outer radius, said first inner conductor inner radius being greater than said second inner conductor outer radius; and said computing said difference later resistivity step further comprises calculating said resistivity from said difference layer resistance $R_i$ and thickness $|\delta_i - \delta_{i-1}|$, said second outer conductor inner radius $r_b$ and said first inner conductor inner radius $r_a$ where said resistivity is given as $$\rho = \frac{2\pi R_{di} |\delta_i - \delta_{i-1}|}{\ln\left(\frac{r_b}{r_a}\right)}.$$

26. The method of claim 24 wherein
said first current electrode comprises a first conductive member in electrical contact with a proximal end of a rod formed from said conductive material;
said first voltage electrode comprises a first ring-shaped conductive member in electrical contact with a first diameter of said rod, said first rod diameter adjacent to said first conductive member at said proximal rod end;
said second current electrode comprises a second conductive member in electrical contact with a distal end of said rod;
said second voltage electrode comprises a second ring-shaped conductive member in electrical contact with a second diameter of said rod, said second rod diameter adjacent to said second conductive member of said distal rod end; and said computing said difference later resistivity step further comprises calculating said resistivity from said sample volume resistance R and depth $\delta$, said rod radius a and said conductive member radius r where said resistivity is given as $$\rho = \frac{\pi \delta R}{\frac{L}{2a} + \ln\left(\frac{a}{r}\right)}.$$

27. The method of claim 21 where said solute is selected from the group consisting of carbon, nitrogen, phosphorus, sulfur, oxygen, arsenic, manganese, molybdenum, nickel, chromium, cobalt, cesium, platinum, palladium, titanium, yttrium, neodymium, boron, oxygen, zirconium, niobium, tantalum, tungsten, and rhenium and said conductive material is selected from a group consisting of ferrous alloys, non-ferrous alloys, transition metal alloys, noble metal alloys, rare earth metal alloys, alkaline earth metal alloys and alloys of aluminum, gallium, germanium, silicon, indium, tin, thallium, lead and bismuth.

28. The method of claim 21 where said solute is carbon and said conductive material is a ferrous alloy.

* * * * *